(12) United States Patent
Frank et al.

(10) Patent No.: US 8,036,441 B2
(45) Date of Patent: Oct. 11, 2011

(54) METHOD AND APPARATUS FOR PERFORMING 2D TO 3D REGISTRATION

(75) Inventors: Kevin J. Frank, Lafayette, CO (US); Kevin E. Mark, Westminster, CO (US)

(73) Assignee: Medtronic Navigation, Inc., Louisville, CO (US)

(*) Notice: Subject to any disclaimer, the term of this patent is extended or adjusted under 35 U.S.C. 154(b) by 0 days.

(21) Appl. No.: 12/535,524

(22) Filed: Aug. 4, 2009

(65) Prior Publication Data
US 2009/0290771 A1 Nov. 26, 2009

Related U.S. Application Data

(63) Continuation of application No. 10/644,680, filed on Aug. 20, 2003, now Pat. No. 7,570,791.

(60) Provisional application No. 60/465,615, filed on Apr. 25, 2003.

(51) Int. Cl.
*G06K 9/00* (2006.01)
(52) U.S. Cl. ............... 382/131; 382/132; 382/294
(58) Field of Classification Search ........... 382/128–132
See application file for complete search history.

(56) References Cited

U.S. PATENT DOCUMENTS

| | | | | |
|---|---|---|---|---|
| 6,144,759 | A * | 11/2000 | Weese et al. | 382/132 |
| 6,381,485 | B1 * | 4/2002 | Hunter et al. | 600/407 |
| 6,466,813 | B1 * | 10/2002 | Shukla et al. | 600/411 |
| 6,470,207 | B1 * | 10/2002 | Simon et al. | 600/426 |
| 6,714,810 | B2 * | 3/2004 | Grzeszczuk et al. | 600/427 |
| 6,947,786 | B2 * | 9/2005 | Simon et al. | 600/427 |
| 6,990,368 | B2 * | 1/2006 | Simon et al. | 600/425 |
| 7,426,318 | B2 * | 9/2008 | Fu et al. | 382/294 |
| 7,606,613 | B2 * | 10/2009 | Simon et al. | 600/426 |
| 7,660,623 | B2 * | 2/2010 | Hunter et al. | 600/424 |
| 2002/0075994 | A1 * | 6/2002 | Shahidi et al. | 378/62 |
| 2002/0077543 | A1 * | 6/2002 | Grzeszczuk et al. | 600/424 |
| 2002/0082492 | A1 * | 6/2002 | Grzeszczuk | 600/407 |
| 2004/0106868 | A1 * | 6/2004 | Liew et al. | 600/442 |
| 2004/0215071 | A1 * | 10/2004 | Frank et al. | 600/407 |
| 2006/0002631 | A1 * | 1/2006 | Fu et al. | 382/294 |

OTHER PUBLICATIONS

Penney et al., "A Comparison of Similarity Measures for Use in a 2D-3D Medical Image Registration" IEEE transactions on Medical Imaging vol. 17 No. 4 Aug. 1998.*

Murphy et al "Automatic six degree of freedom image registration algorithm for image guided frameless sterotaxic radio surgery" American Association of Physics in Medicine 1997.*

* cited by examiner

*Primary Examiner* — Bhavesh Mehta
*Assistant Examiner* — Sean Motsinger
(74) *Attorney, Agent, or Firm* — Harness, Dickey

(57) ABSTRACT

A method and apparatus for performing 2D to 3D registration includes an initialization step and a refinement step. The initialization step is directed to identifying an orientation and a position by knowing orientation information where data images are captured and by identifying centers of relevant bodies. The refinement step uses normalized mutual information and pattern intensity algorithms to register the 2D image to the 3D volume.

20 Claims, 12 Drawing Sheets

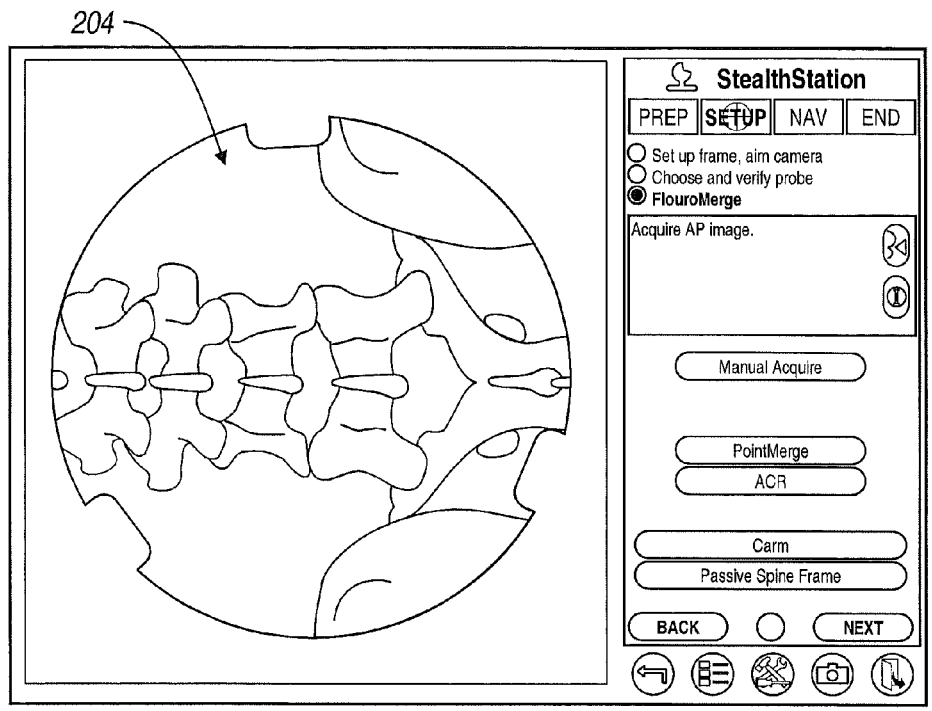
FIG. 6 ACQUIRE AP IMAGE
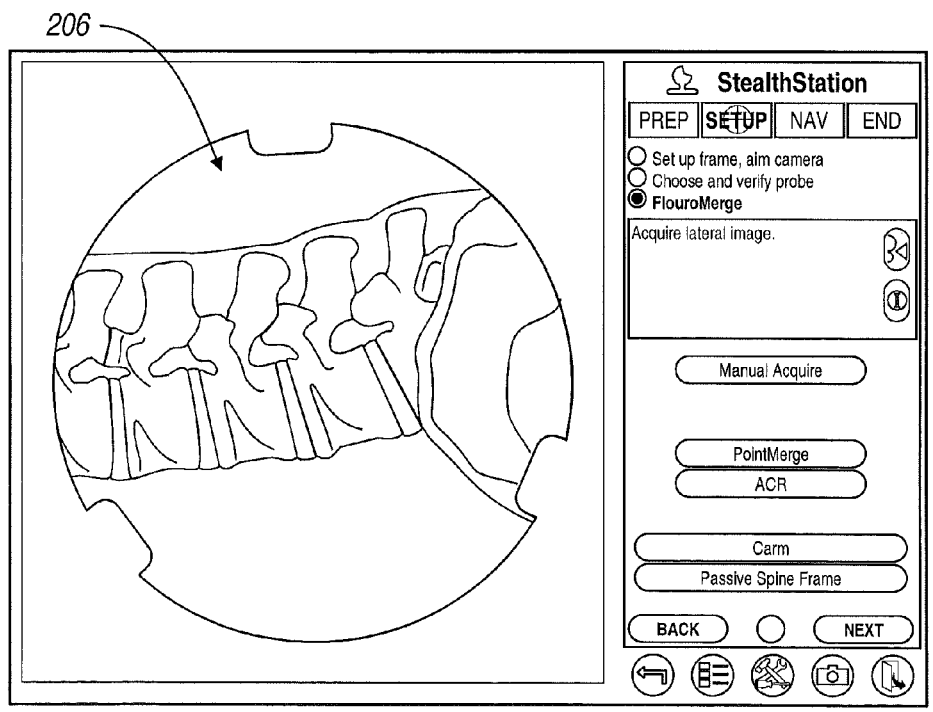
FIG. 7 ACQUIRE LATERAL IMAGE

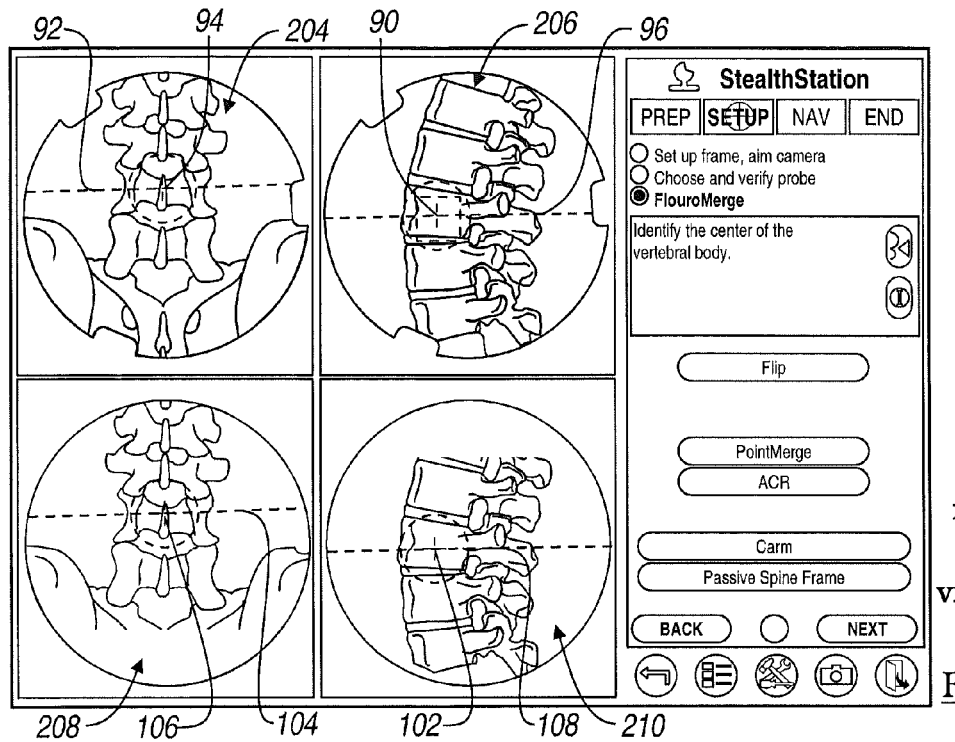
FIG. 12 IDENTIFY CENTER OF VERTEBRAL BODY
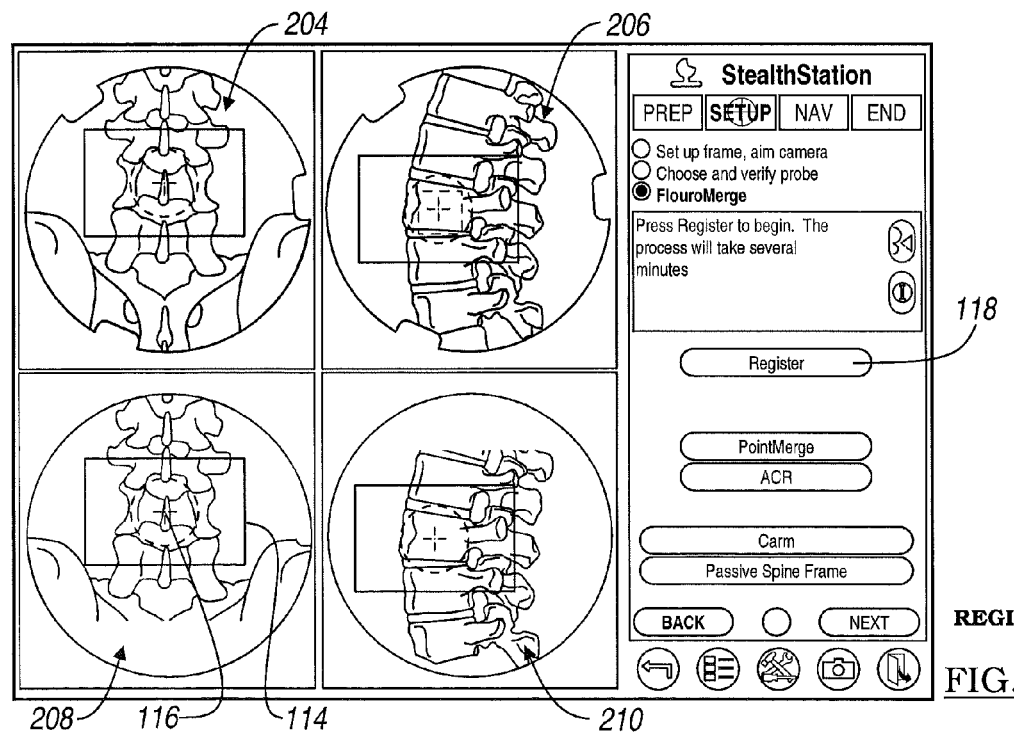
FIG. 13 REGISTER

REGISTRATION COMPLETE

VERIFY REGISTRATION ACCURACY

US 8,036,441 B2

METHOD AND APPARATUS FOR PERFORMING 2D TO 3D REGISTRATION

CROSS-REFERENCE TO RELATED APPLICATIONS

This application is a continuation of U.S. application Ser. No. 10/644,680, filed on Aug. 20, 2003, which claims the benefit of U.S. Provisional Application No. 60/465,615, filed on Apr. 25, 2003. The disclosure of the above application is incorporated herein by reference.

FIELD OF THE INVENTION

The present invention generally relates to image guided surgery, and more specifically, to a method and apparatus for performing two-dimensional to three-dimensional registration of image data used during image guided surgery.

BACKGROUND OF THE INVENTION

Image guided medical and surgical procedures utilize patient images obtained prior to or during a medical procedure to guide a physician performing the procedure. Recent advances in imaging technology, especially in imaging technologies that produce highly-detailed, computer-generated two, three and four-dimensional images, such as computed tomography (CT), magnetic resonance imaging (MRI), isocentric C-arm fluoroscopic imaging, fluoroscopes or ultrasounds have increased the interest in image guided medical procedures. During these image guided medical procedures, the area of interest of the patient that has been imaged is displayed on a display. Surgical instruments and/or implants that are used during the medical procedure are tracked and superimposed onto the display to show the location of the surgical instrument relative to the area of interest in the body.

A example of an image guided surgical navigation system that enables the physician to see the location of an instrument relative to a patient's anatomy, without the need to acquire real-time fluoroscopic images throughout the surgical procedure is generally disclosed in U.S. Pat. No. 6,470,207, entitled "Navigational Guidance Via Computer-Assisted Fluoroscopic Imaging," issued Oct. 22, 2002, which is incorporated herein by reference in its entirety. In this system, representations of surgical instruments are overlaid on pre-acquired fluoroscopic images of a patient based on the position of the instruments determined by a tracking sensor.

Before overlaying a three-dimensional image with graphical representations of surgical instruments, the corresponding points in the three-dimensional image and points in the patient's reference frame must be determined. This procedure is generally known as registration of the image. A representative system that performs image registration is set out in U.S. Pat. No. 6,470,207. The three-dimensional patient specific images can be registered to a patient on the operating room table (surgical space) using multiple two-dimensional image projections. This process is often referred to as 2D/3D registration, which uses spatial transformations that can be established. This transformation is generally between the acquired fluoroscopic images and the three-dimensional image data set, such as CT or MRI images corresponding to the same patient. Once the transformations have been established, it is possible to directly relate the surgical space to both the two-dimensional and three-dimensional image space.

Various ways of achieving 2D to 3D registration by utilizing acquired 2D images to register 3D volume images are known in the art. These types of 2D to 3D registrations include contour algorithms, point registration algorithms, surface registration algorithms, density comparison algorithms, and pattern intensity registration algorithms. These registrations, however, are very computationally tasking and therefore, generally take several minutes to perform the 2D to 3D registration. In fact, some of these registrations can take upwards of twenty minutes to an hour to perform the registration. Moreover, these registration processes may also result in an inaccurate registration after waiting an extensive period of time.

It is, therefore, desirable to provide a method and apparatus for performing 2D to 3D registration in a more accurate and efficient manner, which does not suffer from the above-mentioned disadvantages. It is, therefore, an object of the present invention to provide such a method and apparatus for performing 2D to 3D registration.

SUMMARY OF THE INVENTION

In accordance with the teachings of the present invention, a method and apparatus for use in performing 2D to 3D registration is disclosed. The 2D to 3D registration essentially includes two primary steps, an initialization step and a refinement step. The initialization step can be further broken down into an initial orientation step and an initial position step. In the refinement step, image matching algorithms are used to refine registration, such that all of the coordinate systems involved are subsequently linked after the refinement process is conducted.

In one embodiment, a method for registering two-dimensional image data with three-dimensional image data of a body of interest includes acquiring the three-dimensional image data having the first patient orientation information and acquiring the two-dimensional image data having second patient orientation information. The method further includes generating a digitally reconstructed radiograph that substantially corresponds to the two-dimensional image data using the three-dimensional image data and the first and second patient orientation information.

In another embodiment, a method for registering two-dimensional image data with three-dimensional image data of a body of interest includes acquiring the three-dimensional image data and acquiring the two-dimensional image data. The method further includes generating a digitally reconstructed radiograph using the three-dimensional image data and registering the two-dimensional image data with the three-dimensional image data using a first similarity/cost measure and a second similarity/cost measure.

In yet another embodiment, a method for registering two-dimensional image data with three-dimensional image data of a body of interest includes acquiring the three-dimensional image data of the body of interest and acquiring a two-dimensional image of the body of interest. The method further includes generating a digitally reconstructed radiograph that substantially corresponds to the two-dimensional image, performing intensity adjustment of the two-dimensional image to reduce the effect of an interfering object, and aligning the two-dimensional image with the digitally reconstructed radiograph using a similarity/cost measure.

In another embodiment, a method for registering two-dimensional image data with three-dimensional image data of a body of interest includes acquiring the three-dimensional image data having first patient orientation information, acquiring a first two-dimensional image having second patient orientation information and acquiring a second two-dimensional image having third patient orientation information. The method further includes identifying a center of the body of interest in the first and second images, generating first and second digitally reconstructed radiographs, identifying the center of the body of interest in the first and second digitally reconstructed radiographs and registering the first and second two-dimensional images with the three-dimensional image data using at least a first similarity/cost measure and a second similarity/cost measure.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 4-18 illustrate performing the 2D to 3D registration using the navigation system of FIG. 1;

DETAILED DESCRIPTION OF THE PREFERRED EMBODIMENTS

The following description of the embodiment(s) is merely exemplary in nature and is in no way intended to limit the invention, its application, or uses. Moreover, while the invention is discussed in detail below in regard to performing 2D to 3D registration during a spinal surgical procedure, the present invention may be used with any type of medical procedure, including orthopedic, cardiovascular, neurovascular, soft tissue procedures, or any other medical procedures. Furthermore, while the invention is discussed in detail below with regard to capturing anterior to posterior and lateral images, it should be understood that any two images along two planes may be utilized with the present invention.

Figure 1:
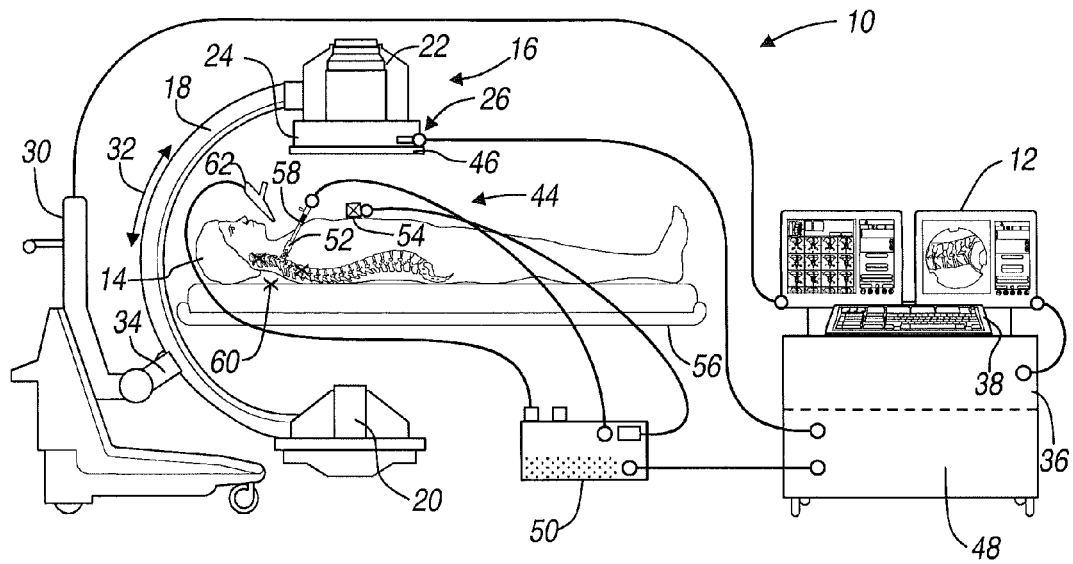
FIG. 1 is a diagram of a navigation system used that performs the 2D to 3D registration according to the teachings of the present invention.

FIG. 1 is a diagram illustrating an image guided navigation system 10 having a display 12 for use in navigating a surgical instrument or implant during a medical procedure. The navigation system 10 may be used to navigate any type of instrument or delivery system, such as a reamer, impactor, cutting block, saw blade, catheter, guide wires, needles, drug delivery systems, and cell delivery systems. The navigation system 10 may also be used to navigate any type of implant including orthopedic implants, spinal implants, cardiovascular implants, neurovascular implants, soft tissue implants, or any other devices implanted in a patient 14. The navigation system 10 may also be used to navigate implants or devices that are formed as an assembly or from multiple components where the location and orientation of each component is dependent upon one another to be effective in its use. For example, during a spinal procedure, the navigation system 10 may be used to track and align a spinal screw with a spinal rod to insure attachment of each device.

The navigation system 10 includes an imaging device 16 that is used to acquire pre-operative or real-time images of the patient 14. The imaging device 16 may be a fluoroscopic C-arm x-ray imaging device that includes a C-arm 18, an x-ray source 20, an x-ray receiving section 22, an optional calibration and tracking target 24 and optional radiation sensors 26. The calibration and tracking target 24 includes calibration markers 28 (see FIGS. 2a-2b), further discussed herein. The calibration and tracking target 24 is used to both calibrate the C-arm imaging device, as well as track the location of the C-arm 18 when an image is captured, also further discussed herein.

A C-arm controller 30 captures the x-ray images received at the receiving section 22 and stores the images for later use. The C-arm controller 30 may also control the rotation of the C-arm 18. For example, the C-arm 18 may move in the direction of arrow 32 or rotate about the long axis of the patient 14, allowing anterior/posterior (AP) or lateral views of the patient 14 to be imaged. Regarding the lateral views of the patient 14, it should be understood that the lateral view can include a lateral/oblique or oblique view where oblique is defined generally as an image orientation of at least 15° rotated from the anterior to posterior (AP) axis about the superior to inferior axis. Each of these movements involve rotation about a mechanical axis 34 of the C-arm 18. In this example, the long axis of the patient 14 is substantially in line with the mechanical axis 34 of the C-arm 18. This enables the C-arm 18 to be rotated relative to the patient 14, allowing various images of the patient 14 to be taken from multiple directions or about multiple planes. An example of a fluoroscopic C-arm x-ray imaging device 16 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, etc.

In operation, the imaging device 16 generates x-rays from the x-ray source 20 that propagate through the patient 14 and calibration and tracking target 24, into the x-ray receiving section 22. The receiving section 22 generates an image representing the intensities of the received x-rays. Typically, the receiving section 22 includes an image intensifier that first converts the x-rays to visible light and a charge coupled device (CCD) video camera that converts the visible light into digital images. Receiving section 22 may also be a digital device that converts x-rays directly to digital images, thus potentially avoiding distortion introduced by first converting to visible light. With this type of digital C-arm, which is generally a flat panel device, the calibration portion of the calibration and tracking target 24 and the calibration process discussed below may be eliminated. Also, the calibration process may be eliminated for different types of medical procedures. Alternatively, the imaging device 16 may only take a single image with the calibration portion of the calibration and tracking target 24 in place. Thereafter, the calibration portion of the calibration and tracking target 24 may be removed from the line-of-sight of the imaging device 16.

Two-dimensional fluoroscopic images taken by the imaging device 16 are captured and stored in the C-arm controller 30. These images are forwarded from the C-arm controller 30 to a controller or work station 36 having the display 12 that may either include a single display 12 or a dual display 12 and a user interface 38. The work station 36 provides facilities for displaying on the display 12, saving, digitally manipulating, or printing a hard copy of the received images, as well as performing the 2D to 3D registration, as further discussed herein. The user interface 38, which may be a keyboard, joy stick, mouse, touch pen, touch screen or other suitable device allows a physician or user to provide inputs to control the imaging device 16, via the C-arm controller 30, or identify centers of a body of interest, further discussed herein. The work station 36 may also direct the C-arm controller 30 to adjust the rotational axis 34 of the C-arm 18 to obtain various two-dimensional images along different planes in order to generate representative two-dimensional and three-dimensional images. Upon obtaining the various two-dimensional images, along different planes, such as the AP and lateral planes, the calibration and tracking target 24 identifies where the C-arm 18 is located. This information is forwarded to the work station 36 for use later in the 2D to 3D registration.

When the x-ray source 20 generates the x-rays that propagate to the x-ray receiving section 22, the radiation sensors 26 sense the presence of radiation, which is forwarded to the C-arm controller 30, to identify whether or not the imaging device 16 is actively imaging. This information is also transmitted to a coil array controller 48, further discussed herein. Alternatively, a person or physician may manually indicate when the imaging device 16 is actively imaging or this function can be built into the x-ray source 20, x-ray receiving section 22, or the control computer 30. Likewise, when the imaging device 16 is actively imaging, the calibration and tracking target 24 identifies the location of the C-arm 18 during the imaging phase, which information is forwarded to both the work station 36 and the coil array controller 48. The calibration and tracking target 24 may include any type of location sensor to identify the location of the C-arm 18, such as an optical sensor that can be received by an optical navigation device to determine the location of the C-arm 18.

Figure 2A:
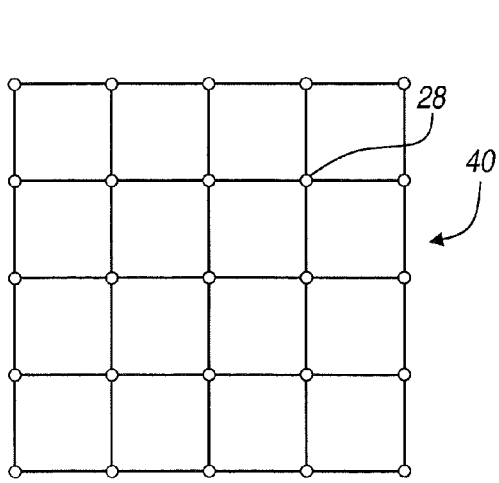
FIGS. 2a and 2b are diagrams representing undistorted and distorted views of a fluoroscopic C-arm imaging device.
Figure 2B:
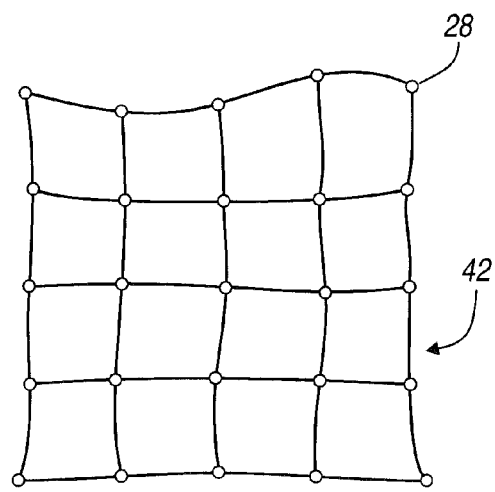

Fluoroscopic C-arm imaging devices 16 that do not include a digital receiving section 22 generally require the calibration and tracking target 24. This is because the raw images generated by the receiving section 22 tend to suffer from undesirable distortion caused by a number of factors, including inherent image distortion in the image intensifier and external electromagnetic fields. An empty undistorted or ideal image and an empty distorted image are shown in FIGS. 2a and 2b, respectively. The checkerboard shape, shown in FIG. 2a, represents the ideal image 40 of the checkerboard arranged calibration markers 28. The image taken by the receiving section 22, however, can suffer from distortion, as illustrated by the distorted calibration marker image 42, shown in FIG. 2b.

Intrinsic calibration, which is the process of correcting image distortion in a received image and establishing the projective transformation for that image, involves placing the calibration markers 28 in the path of the x-ray, where the calibration markers 28 are opaque or semi-opaque to the x-rays. The calibration markers 28 are rigidly arranged in pre-determined patterns in one or more planes in the path of the x-rays and are visible in the recorded images. Because the true relative position of the calibration markers 28 in the recorded images are known, the C-arm controller 30 or the work station or computer 36 is able to calculate an amount of distortion at each pixel in the image (where a pixel is a single point in the image). Accordingly, the computer or work station 36 can digitally compensate for the distortion in the image and generate a distortion-free or at least a distortion improved image 40 (see FIG. 2a). A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the fluoroscopic C-arm imaging device 16 is shown in FIG. 1, any other alternative imaging modality may also be used. For example, isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), 2D, 3D or 4D ultrasound, intraoperative CT, or MRI may also be used to acquire pre-operative or real-time images or image data of the patient 14. Image datasets from hybrid modalities, such as positron emission tomography (PET) combined with CT, or single photon emission computer tomography (SPECT) combined with CT, could also provide functional image data superimposed onto anatomical data to be used to confidently reach target sights within the areas of interest. It should further be noted that the fluoroscopic C-arm imaging device 16, as shown in FIG. 1, provides a virtual bi-plane image using a single-head C-arm fluoroscope 16 by simply rotating the C-arm 18 about at least two planes. These planes could be orthogonal planes (i.e., AP and lateral views) to generate two-dimensional images that can be converted to three-dimensional volumetric images or registered to pre-acquire three-dimensional volumetric images.

The navigation system 10 further includes an electromagnetic navigation or tracking system 44 that includes a transmitter coil array 46, the coil array controller 48, a navigation probe interface 50, an instrument 52 having an electromagnetic tracker and a dynamic reference frame 54. It should further be noted that the entire tracking system 44 or parts of the tracking system 44 may be incorporated into the imaging device 16, including the work station 36 and radiation sensors 26. Incorporating the tracking system 44 will provide an integrated imaging and tracking system. Any combination of these components may also be incorporated into the imaging system 16, which again can include a fluoroscopic C-arm imaging device or any other appropriate imaging device.

The transmitter coil array 46 is shown attached to the receiving section 22 of the C-arm 18. However, it should be noted that the transmitter coil array 46 may also be positioned at any other location as well. For example, the transmitter coil array 46 may be positioned at the x-ray source 20, within the OR table 56 positioned below the patient 14, on siderails associated with the OR table 56, or positioned on the patient 14 in proximity to the region being navigated, such as by the patient's pelvic area. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 drives each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induces currents in sensors 58 positioned in the instrument 52, further discussed herein. These induced signals from the instrument 52 are delivered to the navigation probe interface 50 and subsequently forwarded to the coil array controller 48. The navigation probe interface 50 provides all the necessary electrical isolation for the navigation system 10. The navigation probe interface 50 also includes amplifiers, filters and buffers required to directly interface with the sensors 58 in instrument 52. Alternatively, the instrument 52 may employ a wireless communications channel as opposed to being coupled directly to the navigation probe interface 50.

The instrument 52 is equipped with at least one, and may include multiple localization sensors 58. In this regard, the instrument 52 may include an orthogonal pair coil sensor 58 or a tri-axial coil sensor 58 or multiple single coil sensors 58 positioned about the instrument 52. Here again, the instrument 52 may be any type of medical instrument or implant. For example, the instrument may be a catheter that can be used to deploy a medical lead, be used for tissue ablation, or be used to deliver a pharmaceutical agent. The instrument 52 may also be an orthopedic instrument, used for an orthopedic procedure, such as reamers, impactors, cutting blocks, saw blades, drills, etc. The instrument 52 may also be any type of neurovascular instrument, cardiovascular instrument, soft tissue instrument, etc. Finally, the instrument 52 may be an implant that is tracked, as well as any other type of device positioned and located within the patient 14. These implants can include orthopedic implants, neurovascular implants, cardiovascular implants, soft tissue implants, or any other devices that are implanted into the patient 14. Particularly, implants that are formed from multiple components where the location and orientation of each component is dependent upon the location and orientation of the other component, such that each of these components can be tracked or navigated by the navigation and tracking system 44 to be displayed on the display 12.

In an alternate embodiment, the electromagnetic sources or generators may be located within the instrument 52 and one or more receiver coils may be provided externally to the patient 14 forming a receiver coil array similar to the transmitter coil array 46. In this regard, the sensor coils 58 would generate electromagnetic fields, which would be received by the receiving coils in the receiving coil array similar to the transmitter coil array 46. Other types of localization or tracking may also be used with other types of navigation systems, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. These types of localization systems include conductive, active optical, passive optical, ultrasound, sonic, electromagnetic, etc. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 54 of the electromagnetic tracking system 44 is also coupled to the navigation probe interface 50 to forward the information to the coil array controller 48. The dynamic reference frame 54 is a small magnetic field detector or any other type of detector/transmitter that is designed to be fixed to the patient 14 adjacent to the region being navigated so that any movement of the patient 14 is detected as relative motion between the transmitter coil array 46 and the dynamic reference frame 54. This relative motion is forwarded to the coil array controller 48, which updates registration correlation and maintains accurate navigation. The dynamic reference frame 54 can be configured as a pair of orthogonally oriented coils, each having the same center or may be configured in any other non-coaxial coil configuration. The dynamic reference frame 54 may be affixed externally to the patient 14, adjacent to the region of navigation, such as the patient's spinal region, as shown in FIG. 1 or on any other region of the patient. The dynamic reference frame 54 can be affixed to the patient's skin, by way of a stick-on adhesive patch. The dynamic reference frame 54 may also be removably attachable to fiducial markers 60 also positioned on the patient's body and further discussed herein.

Alternatively, the dynamic reference frame 54 may be internally attached, for example, to the spine or vertebrae of the patient using bone screws that are attached directly to the bone. This provides increased accuracy since this will track any motion of the bone. Moreover, multiple dynamic reference frames 54 may also be employed to track the position of two bones relative to a joint. For example, one dynamic reference frame 54 may be attached to a first vertebra, while a second dynamic reference frame 54 may be attached to a second vertebra. In this way, motion of the spine or vertebrae may be detected by the dual dynamic reference frames 54. An exemplary dynamic reference frame 54 and fiducial marker 60, is set forth in U.S. Pat. No. 6,381,485, entitled "Registration of Human Anatomy Integrated for Electromagnetic Localization," issued Apr. 30, 2002, which is hereby incorporated by reference.

Briefly, the navigation system 10 operates as follows. The navigation system 10 creates a translation map between all points in the radiological image generated from the imaging device 16 and the corresponding points in the patient's anatomy in patient space. The navigation system 10 may also perform 2D to 3D registration. That is, 3D image data from a 3D scan, such as a CT scan, can be registered to the 2D fluoroscopic images from the imaging device 16. In this way, simultaneous navigation of both the 3D and the 2D images may also be illustrated on the display 12. After this map is established, whenever a tracked instrument 52 is used, the work station 36 in combination with the coil array controller 48 and the C-arm controller 30 uses the translation map to identify the corresponding point on the pre-acquired image, which is displayed on display 12. This identification is known as navigation or localization. An icon representing the localized point or instrument is shown on the display 12.

To enable navigation, the navigation system 10 detects both the position of the patient's anatomy 14 and the position of the surgical instrument 52. Knowing the location of these two items allows the navigation system 10 to compute and display the position of the instrument 52 in relation to the patient 14. The tracking system 44 is employed to track the instrument 52 and the anatomy simultaneously. While the display 12 is configured to show the instrument.

The tracking system 44 essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the instrument 52 by measuring the field strength at the sensor 58 location. The dynamic reference frame 54 is fixed to the patient 14 to identify the location of the patient 14 in the navigation field. The electromagnetic tracking system 44 continuously recomputes the relative position of the dynamic reference frame 54 and the instrument 52 during localization and relates this spatial information to patient registration data to enable image guidance of the instrument 52 within the patient 14.

Patient registration is the process of determining how to correlate the position of the instrument 52 on the patient 14 to the position on the diagnostic, pre-acquired, or real-time images. To register the patient 14, the physician or user will select and store particular points from the pre-acquired images and then touch the corresponding points on the patient's anatomy with a pointer probe 62. The navigation system 10 analyzes the relationship between the two sets of points that are selected and computes a match, which correlates every point in the image data with its corresponding point on the patient's anatomy or the patient space. The points that are selected to perform registration are the fiducial arrays or landmarks 60. Again, the landmarks or fiducial points 60 are identifiable on the images and identifiable and accessible on the patient 14. The landmarks 60 can be artificial landmarks 60 that are positioned on the patient 14 or anatomical landmarks 60 that can be easily identified in the image data. The system 10 may also perform 2D to 3D registration by utilizing the acquired 2D images to register 3D volume images according to the teachings of the present invention.

In order to maintain registration accuracy, the navigation system 10 continuously tracks the position of the patient 14 during registration and navigation. This is necessary because the patient 14, dynamic reference frame 54, and transmitter coil array 46 may all move during the procedure, even when this movement is not desired. Therefore, if the navigation system 10 did not track the position of the patient 14 or area of the anatomy, any patient movement after image acquisition would result in inaccurate navigation within that image. The dynamic reference frame 54 allows the electromagnetic tracking device 44 to register and track the anatomy. Because the dynamic reference frame 54 is rigidly fixed to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

It should also be understood that localization and registration data may be specific to multiple targets. For example, should a spinal procedure be conducted, each vertebra may be independently tracked and the corresponding image registered to each vertebra. In other words, each vertebra would have its own translation map between all points in the radiological image and the corresponding points in the patient's anatomy in patient space in order to provide a coordinate system for each vertebra being tracked. The tracking system 44 would track any motion in each vertebra by use of a tracking sensor 58 associated with each vertebra. In this way, dual displays 12 may be utilized, where each display tracks a corresponding vertebra using its corresponding translation map and a surgical implant or instrument 52 may be registered to each vertebra and displayed on the display 12 further assisting an alignment of an implant relative to two articulating or movable bones. Moreover, each separate display in a dual display 12 may superimpose the other vertebra so that it is positioned adjacent to the tracked vertebra thereby adding a further level of information.

Figure 3:
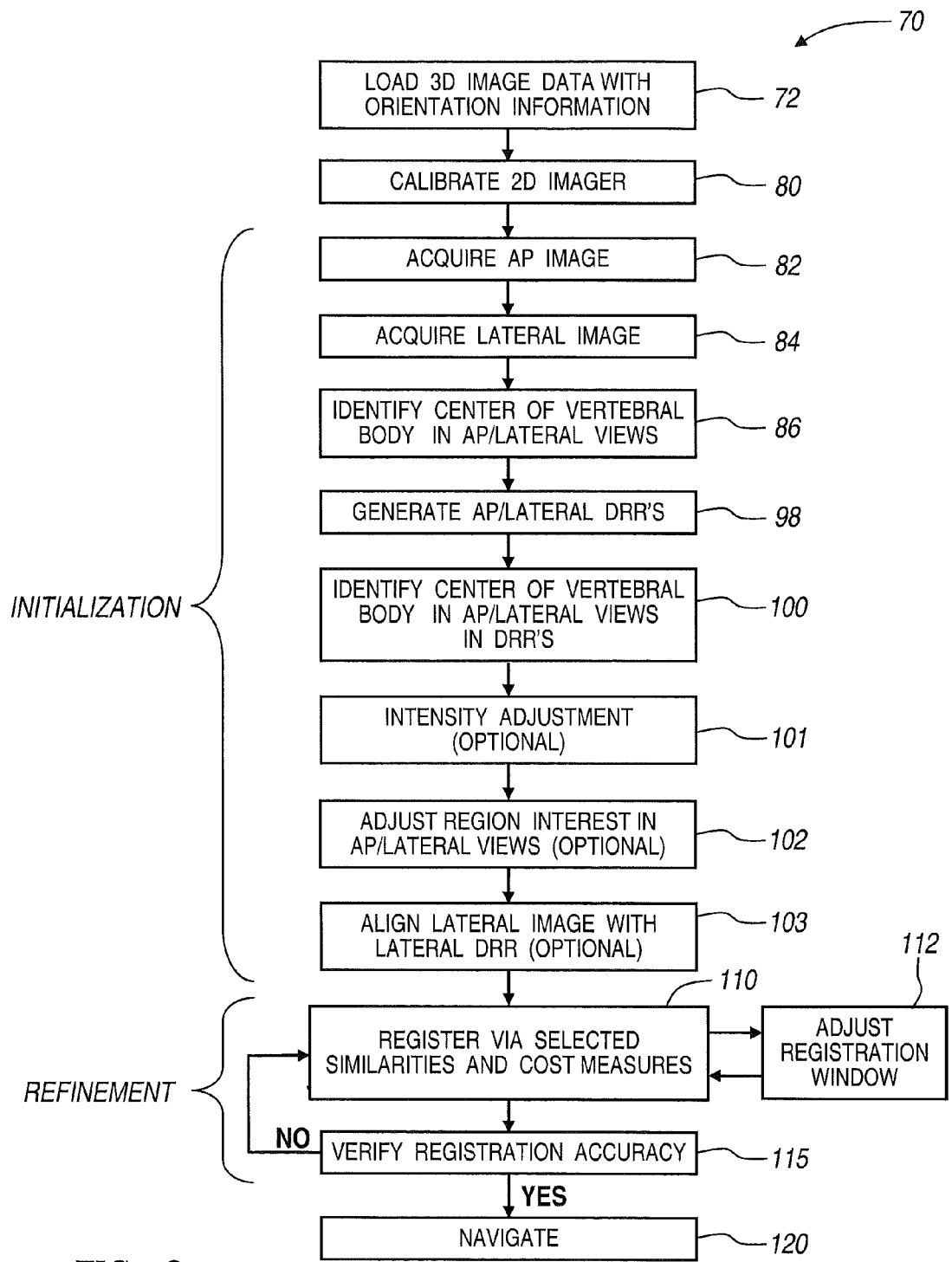
FIG. 3 is a logic block diagram illustrating a method for employing the 2D to 3D registration according to the teachings of the present invention.

Turning to FIG. 3, a two-dimensional to three-dimensional registration method 70 according to the teachings of the present invention is illustrated. Briefly, the 2D to 3D registration can be broken down essentially into two processes or steps (i.e., an initialization step and a refinement step). The initialization step can be broken down further into an initial orientation step and an initial position step. As a first step, we ask the surgeon to acquire a first image or an anterior/posterior (AP) image and a second image or a lateral image from the imaging device 16. These images are used for refinement and navigation, but also to initialize the orientation. Since the imaging device 16 includes the calibration and tracking target 24, the location of the C-arm 18 during image acquisition with respect to the patient coordinate system is known (i.e., patient AP direction and patient lateral direction). This knowledge is combined with the knowledge of how the patient 14 is oriented during the three-dimensional volume scan, such as a CT scan to arrive at an estimate of the patient's orientation with respect to the dynamic reference frame 54. Given the estimated orientation, digitally reconstructed radiographs (DRRs) are created from the CT scan that correspond to the actual interoperative AP and lateral radiographs. The surgeon is presented with the DRRs and the actual radiographs and is asked to identify a common point in all four images. This step provides a common point or position in the CT image data and the dynamic reference frame or patient space coordinates. Once the position and orientation of the patient in the 3D data set and the dynamic reference frame coordinates are known, the method proceeds to the refinement step. After refinement, all of the systems involved are linked and known.

During the initialization step, the surgeon is asked to acquire AP and lateral radiographs or radiographs along any two planes using the imaging device 16. In a spinal procedure, the surgeon is then prompted to identify the center of the vertebral body that the surgeon is interested in. Putting together all of this information, a very good estimate of the orientation and the position is known and is used to compute the DRRs that correspond closely to the actual radiographs for an initial 2D to 3D registration. These DRRs are created using the three dimensional data from the CT scan combined with the information from the C-arm localization target. This information includes patient orientation information gathered during the three-dimensional scan and patient orientation gathered during obtaining the radiographs.

In the refinement step, software is used to provide image matching algorithms that refine the 2D to 3D registration. The software is used to change the initial position and orientation in such a way as to minimize differences between the DRRs and the actual radiographs, thus refining the registration. In the refinement step, similarity or cost measures are used to identify how well the images match. An iterative refinement algorithm changes the initial position and orientation parameters simultaneously to maximize the similarity between the DRRs and the actual radiographs. The similarity or cost measures that are used are selected from known similarity and cost measures, such as normalized mutual information, mutual information, gradient difference algorithms, surface contour algorithms, and pattern intensity algorithms. At least two of the similarity or cost measures are selected and optimized, as further discussed herein. This procedure results in an efficient and accurate way to provide 2D to 3D registration.

Figure 4:
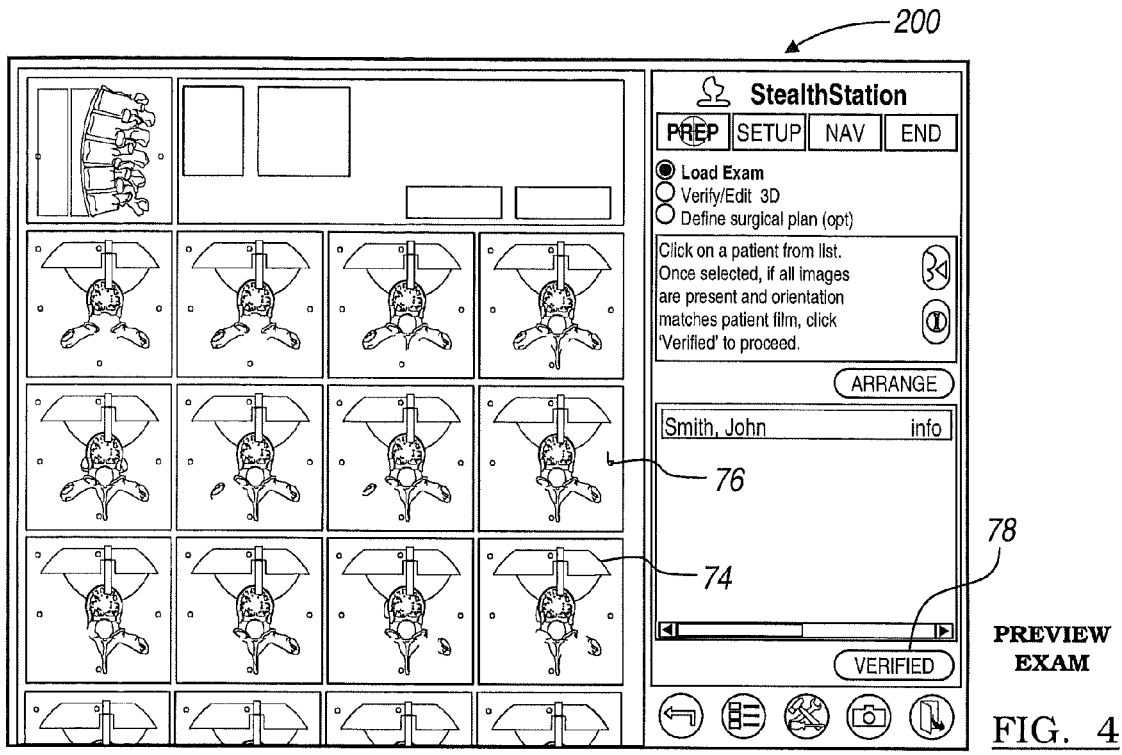

In further detail, the 2D to 3D registration process 70 loaded and processed within the work station 36 begins at block 72 where three dimensional image data 200 having patient orientation information is loaded into the work station 36. FIG. 4 illustrates an exemplary 3D image data set 200 resulting from a CT scan being loaded into the work station 36. It should be noted that while the scan is shown loading information regarding a spinal scan, this 2D to 3D registration may be performed on any portion of the patient's anatomy. Each CT scan slice 74 includes patient orientation information 76. This orientation information identifies the orientation of the patient 14 relative to the scan, such as anterior and posterior orientation, as well as the right and left or medial/lateral orientation of each vertebrae slice in the CT scan. It should also be understood that any other orientation of the region of interest may be utilized and identified with each slice in the CT scan or with any other imaging modality. With all of the 3D image data 200 imported, the surgeon will select the verified button 78 to proceed.

Figure 5:
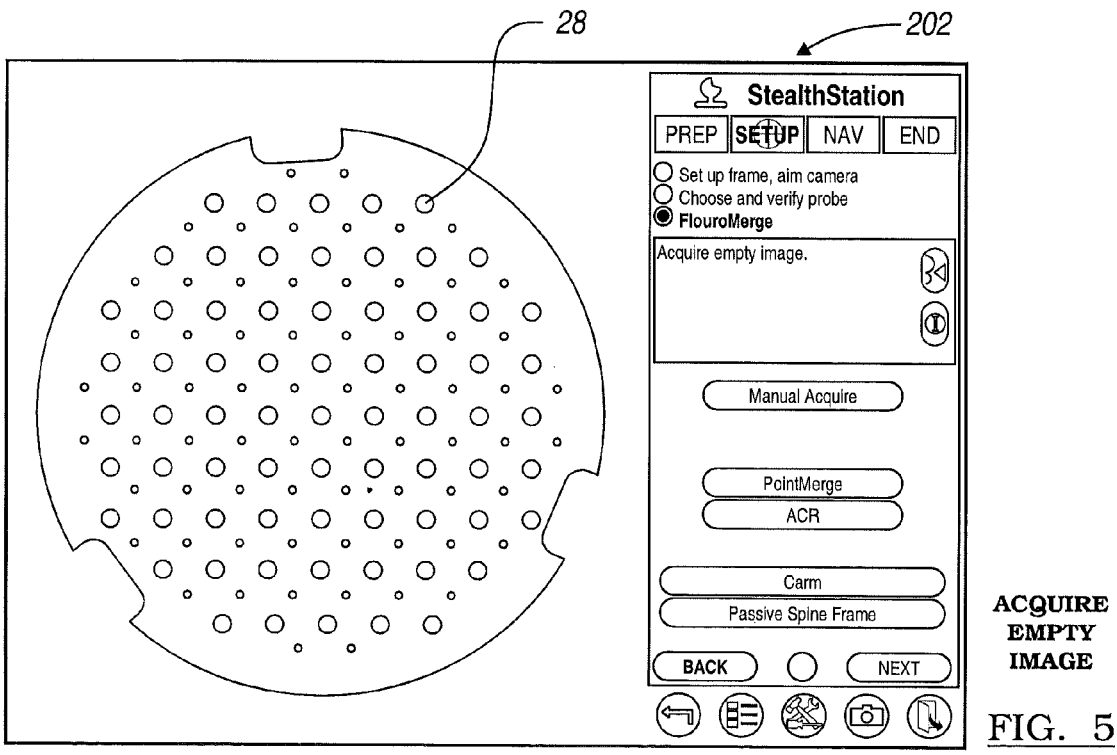

The method then proceeds to block 80 where the fluoroscopic imaging device 16 is calibrated. At calibration block 80, the imaging device 16 acquires an empty image 202, as shown in FIG. 5. The acquisition of the empty image 202 as shown in FIG. 5 is similar to the calibration process, shown in FIGS. 2a and 2b. In this regard, an x-ray is taken by the imaging device 16 and intrinsic calibration is performed on this empty image 202 to calibrate the imaging device 16 using the calibration markers 28. Again, it should be noted that the calibration process is an optional process, depending on the medical procedure conducted or depending on the type of imaging device 16.

Once the imaging device 16 has been calibrated, the patient 14 is positioned within the imaging device 16 to capture various two-dimensional views of the patient. At block 82, a first image or an anterior to posterior (AP) image data 204 is acquired, as shown in FIG. 6. The method then proceeds to block 84 where a second image or a lateral fluoroscopic image data 206 is acquired, as shown in FIG. 7. It should be noted that while the method discloses acquiring an AP image 204 and a lateral image 206, it should be noted that images along any two planes generally 90° apart are acceptable for this method. Alternatively, any images along any two planes may also be acceptable for this method and not necessarily 90° apart. It should again also be pointed out that the lateral image may also be considered a lateral/oblique image, where oblique is defined as an image orientation of at least 15° rotated from the anterior to posterior axis about the superior to inferior axis. It should further be pointed out that when the AP image 204 is acquired at block 82 and the lateral image 206 is acquired at block 84, the calibration and tracking target 24 is used to identify where the C-arm 18 is located relative to the patient 14 during each imaging cycle, thereby providing patient orientation information (i.e., AP and lateral) of the image relative to the patient 14 during each acquisition.

Figure 8:
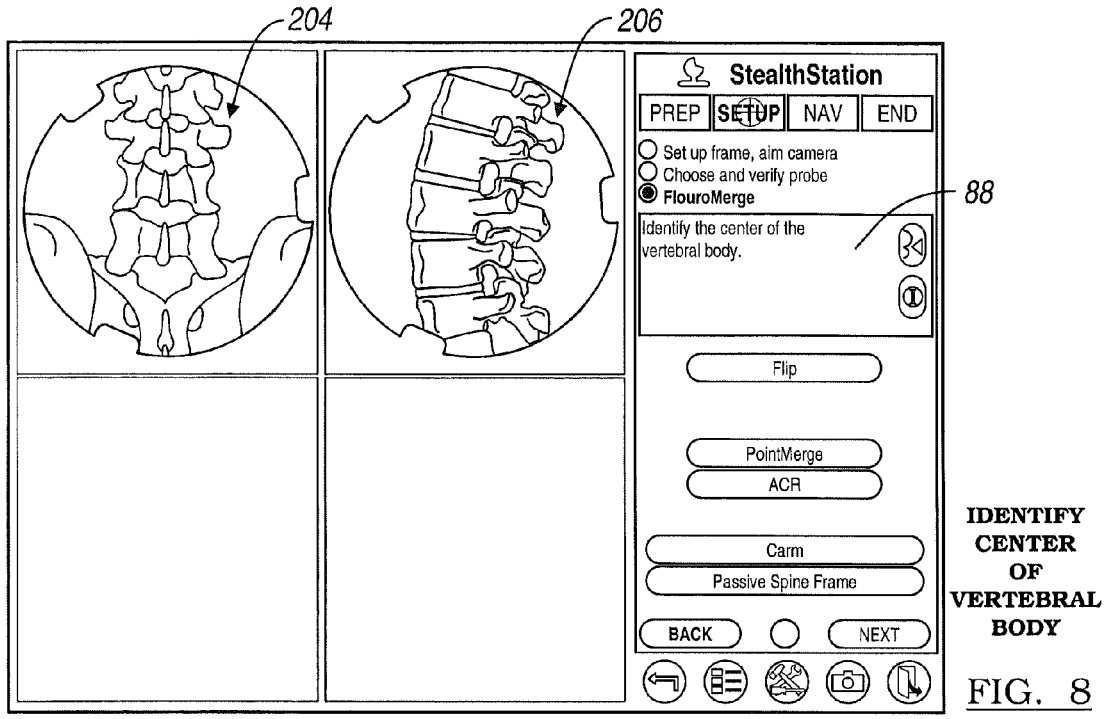
Figure 9:
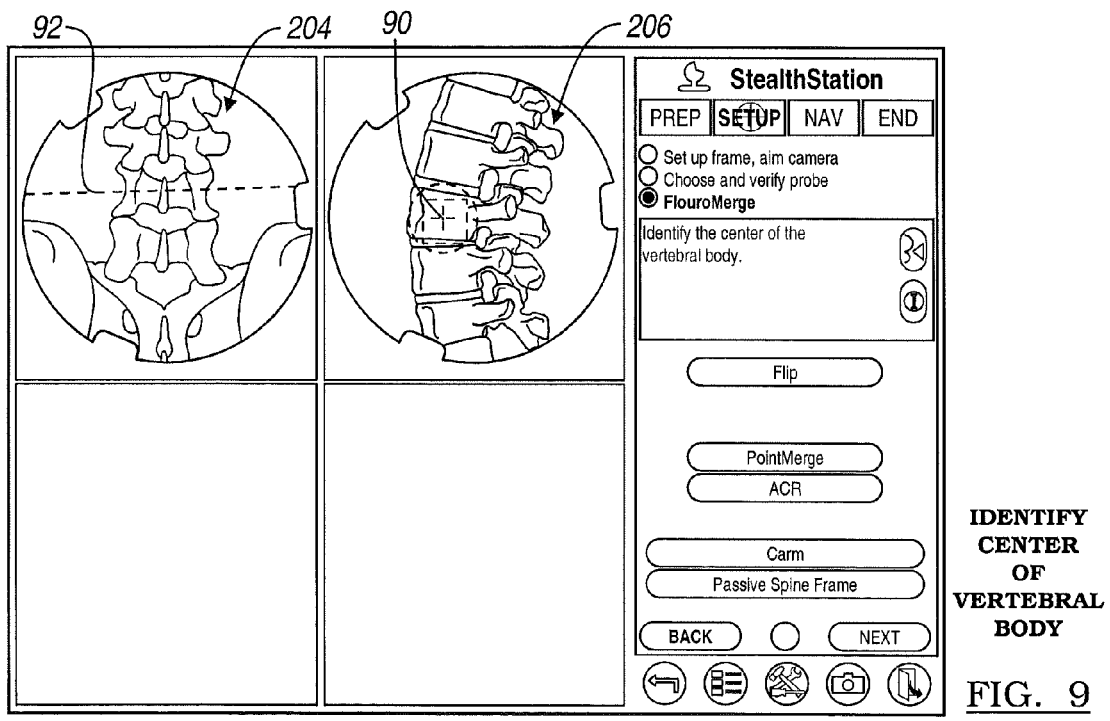
Figure 10:
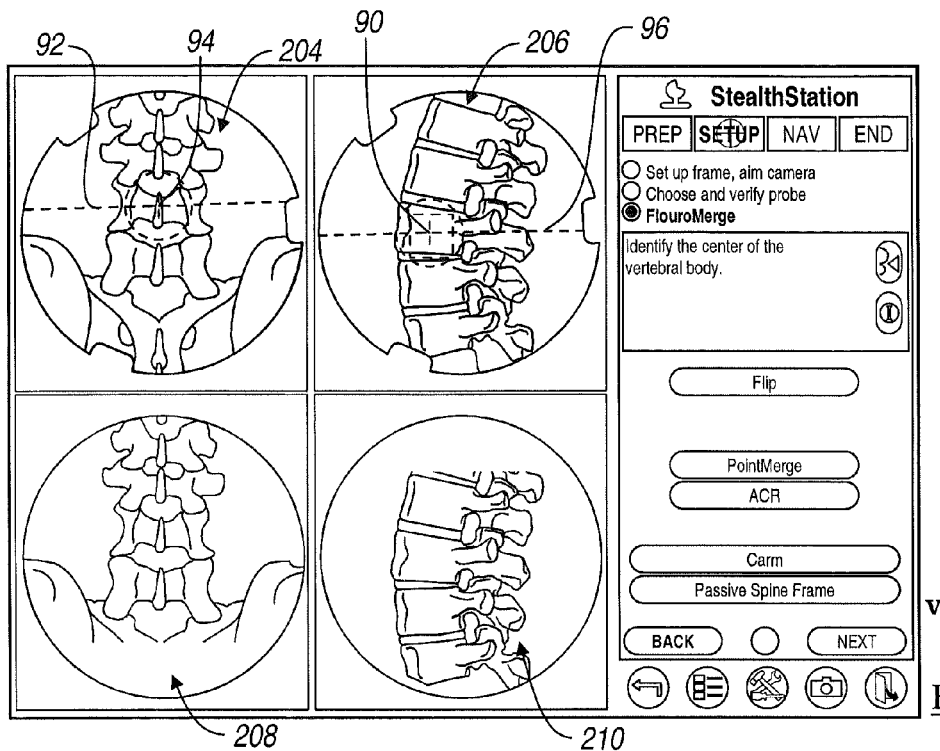

At block 86, the surgeon is prompted to identify the center of the vertebral body in the previously acquired AP image 204 and lateral image 206 or in whatever first and second image was acquired. As illustrated in FIG. 8, both the AP image 204 and lateral image 206 are displayed on the display 12 with the surgeon being prompted in box 88 to identify the center of the vertebral body of interest. As shown in FIG. 9, the surgeon will simply move a target or crosshairs 90 to the perceived center of the desired vertebrae and click the button on a mouse or actuate other devices to identify the center. This creates a line or plane 92 in the anterior/posterior image 204. The surgeon may use a mouse, touch screen, keyboard, touch pen, or any other device 38 to identify the center of the desired vertebral body. Once selected, the plane 92 is illustrated to provide further feedback to the surgeon of the surgeon's selection. If the surgeon is not satisfied with the selection, the surgeon may simply move the crosshairs 90 to another location and enter it to further observe the location of the plane 92 until a satisfactory selection has been made.

The surgeon will then position another crosshair or target 94 on the AP image 204 and enter this target to create another plane 96 in the lateral image 206. The plane 96 lines up with the target 90, providing a visual indication on whether the surgeon has substantially identified the center of the desired vertebrae. It should also be pointed out that the 2D to 3D procedure 70 can use atlas maps to provide an initial estimate for the center of the vertebral body. The surgeon can then simply confirm the estimated center in both the lateral image 206 and AP image 204. These types of estimating tools will provide an automated 2D segmentation, 2D atlas map, or two-dimensional template that can be sized to correspond to the selected vertebrae. Once the template has been sized to the selected vertebrae, the center of this sized two-dimensional template can be calculated and illustrated on the display 12. The surgeon will then simply confirm this center by positioning the crosshairs 90 on the centers and acknowledging the estimate by clicking or actuating on the estimated centers.

Figure 11:
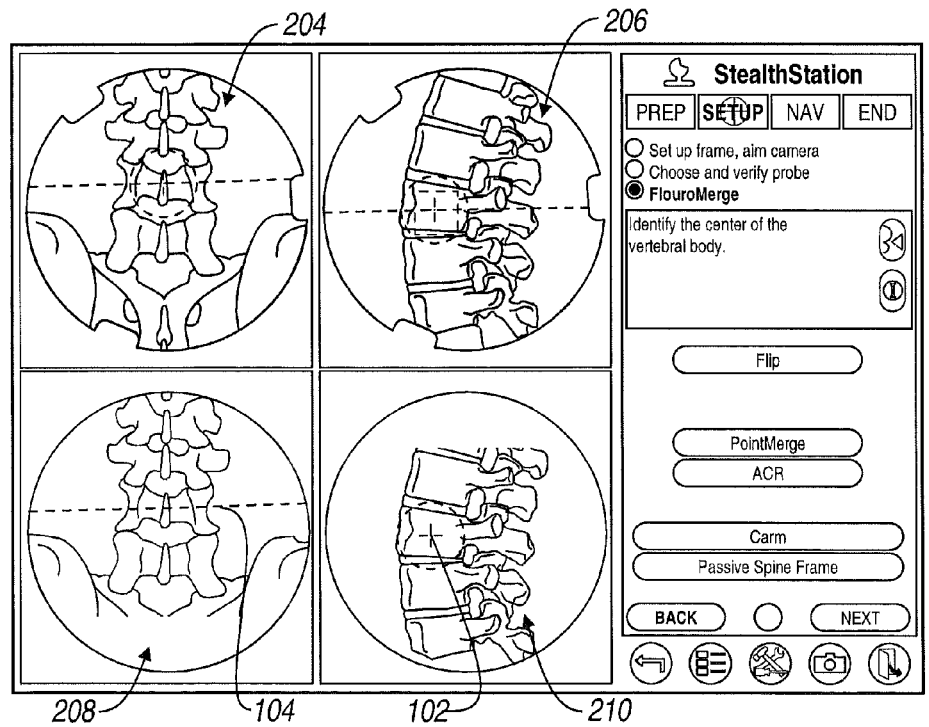

At block 98, AP 208 and lateral 210 digitally reconstructed radiographs (DRRs) are generated, as shown in FIG. 11. By combining the knowledge of where the patient 14 was positioned or oriented relative to the imaging device 16 during image acquisition and how the patient 14 was oriented during the CT scan, an estimate of the patient's orientation with respect to the dynamic reference frame 54 is determined. Using this estimate of the orientation, the digitally reconstructed radiographs 208 and 210 from the 3D CT scan are created to correspond substantially to the actual interoperative radiographs 204 and 206. By using the patient orientation information from the 3D image data with the patient orientation information on the location of the C-arm 18, this information is used in combination with known DRR algorithms to create the DRR. In other words, since it is known where the fluoroscopic scans were taken, and you know the right/left and AP directions of the CT data or any other directions, you take a view through the 3D volume data, along the direction of the fluoroscopic scan and a very accurate DRR is obtained. The DRR is essentially a 2D image taken from a 3D volume where a view through the 3D volume is generated by looking through your 3D volume from the proper orientation or perspective, to create a line for every pixel. Each line is averaged to create a new pixel value, which generates the DRR.

From block 98, the method proceeds to block 100 where again the surgeon identifies the center of the vertebral body of interest in the AP image 208 and lateral image 210 in the DRRs. Again, any two images along any two planes may be used to create the DRRs As shown in FIG. 11, the surgeon again positions a cross-hair or target 102 on the lateral image 210 and selects the proper position, which generates the 2D plane 104 in the AP image 208. The surgeon then positions another cross-hair target 106 on the AP image 208 to generate a 2D plane 108 in the lateral image 210, as shown in FIG. 12. This step again provides a common point or position in the CT image data and the dynamic reference frame or patient space coordinates. Once the initial orientation and position of the patient in the 3D image data and the 2D image data (dynamic reference frame coordinates) are known, the method either proceeds to optional block 101, 102 or 103, or simply proceeds directly to the refinement phase at block 110.

At optional block 101, an optional intensity adjustment is performed on the acquired AP and lateral fluoroscopic images. In this regard, typically when the 2D fluoroscopic images, such as the AP image 82 and the lateral image 84 are acquired, a dynamic reference frame 54 is generally captured in these fluoroscopic images. Since the dynamic reference frame 54 is generally made of metal, it appears as a dark or blackened object in a fluoroscopic image and also makes the surrounding soft tissue brighter. If you review an intensity histogram of the resultant fluoroscopic image, the overall intensity of entire fluoroscopic image is skewed to the right, because of the dynamic reference frame captured in the fluoroscopic image. Therefore, it is desirable to make the acquired fluoroscopic images look more like the generated DRRs 98 because the DRRs are generated from the 3D CT scans that do not include the dynamic reference frame 54. Thus, the DRRs typically do not exhibit a skewing of intensity distribution, based on the intensity interference of the dynamic reference frame 54. The optional intensity adjustment step 101 is used to reduce or eliminate the effect of the dynamic reference frame 54 during the registration process.

Figure 19:
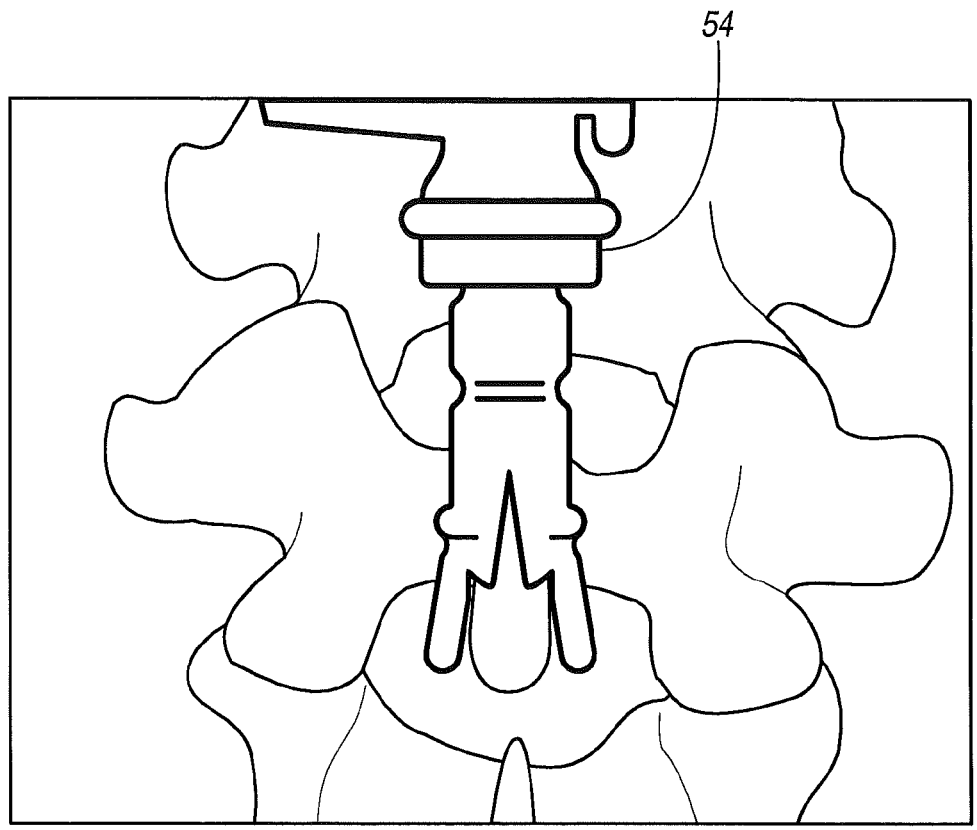
FIG. 19 illustrates a fluoroscopic image before intensity adjustment.
Figure 20:
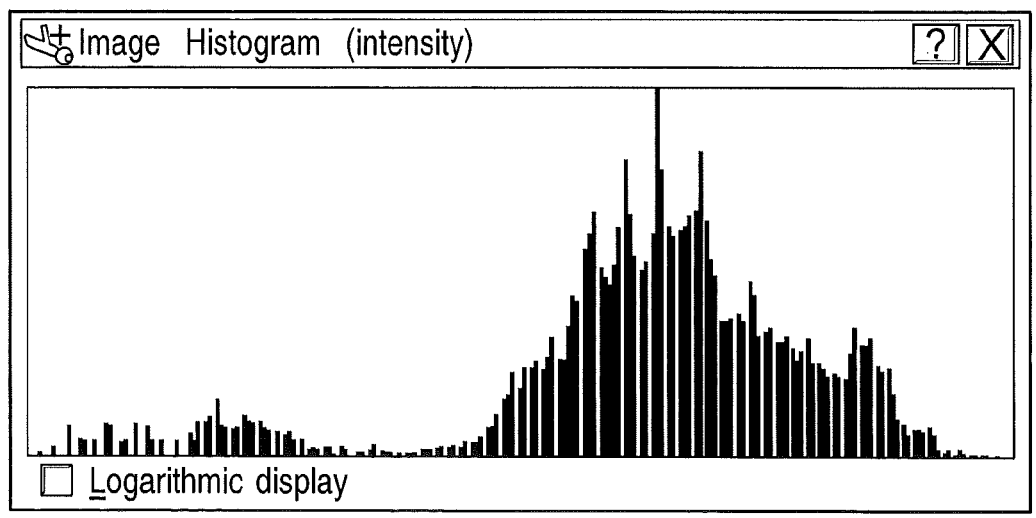
FIG. 20 illustrates an image histogram of the intensity of the fluoroscopic image of FIG. 19.

For example, referring to FIG. 19, an acquired fluoroscopic image that includes the dynamic reference frame 54 before image intensity adjustment 101 has been performed is illustrated. It will be noted upon review of the fluoroscopic image in FIG. 19 that the bone and soft tissue is slightly washed out or brighter because of the presence of the dynamic reference frame 54. FIG. 20 illustrates an image histogram of the intensity of the fluoroscopic image, illustrated in FIG. 19. The horizontal axis of the image histogram is the intensity linearly mapped between 0 and 255 and the vertical axis represents the number of pixels that have that intensity value. Upon review of FIG. 20, it should be noted that the image intensity is skewed to the right illustrating a higher overall image intensity, due to the dynamic reference frame 54. The image histogram of FIG. 20 is a linear mapping of the intensities of the fluoro image that corresponds to brightness or contrast controls, also known as level or width controls, as is known in the art.

Figure 21:
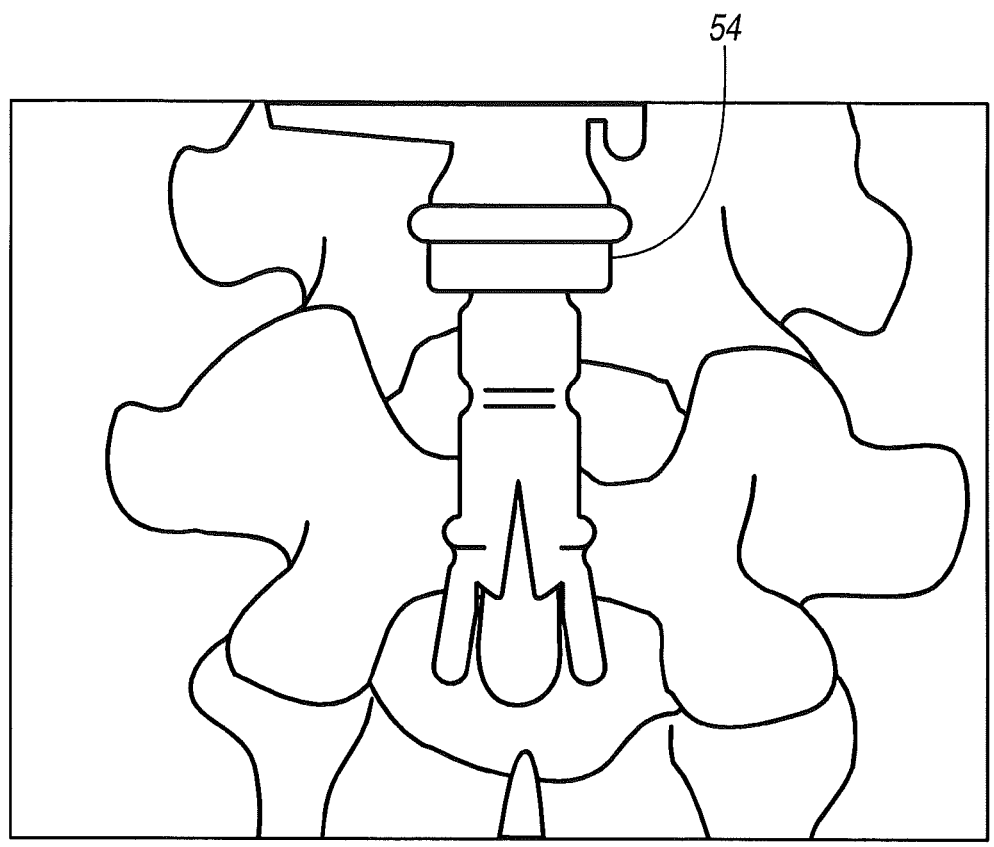
FIG. 21 illustrates a fluoroscopic image after intensity adjustment.
Figure 22:
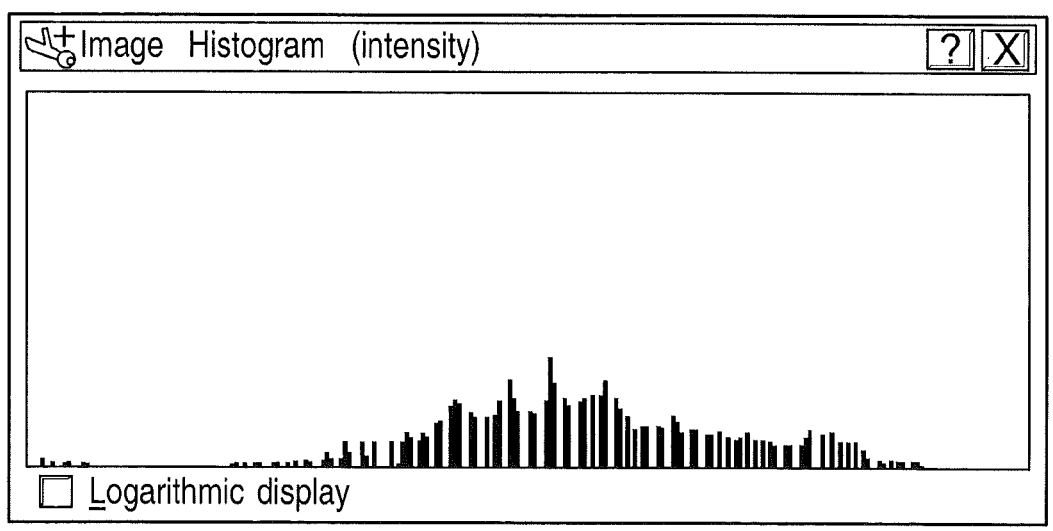
FIG. 22 illustrates an image histogram of the intensity of the fluoroscopic image of FIG. 21.

The optional intensity adjustment step 101 begins by creating the image histogram, illustrated in FIG. 20, which illustrates the image intensity of one of the fluoroscopic images, illustrated in FIG. 19. From this image histogram, a mean intensity value is calculated. Once the mean intensity level has been calculated, the brightness and contrast controls or level and width settings are adjusted, such that the mean intensity is adjusted to a target intensity. For example, the target intensity may be 127, which sets the intensity in the middle of the scale. By adjusting the mean to the target intensity, the image intensity is shifted more to the center of the graph, as illustrated in FIG. 22. This intensity adjustment provides an enhanced image or more contrast for the fluoroscopic image, as illustrated in FIG. 21. That is, the intensity adjusted fluoroscopic image in FIG. 21 provides more contrast similar to the DRRs and is also able to substantially reduce or eliminate the brightness effect of the dynamic reference frame 54 in the fluoroscopic image. Thus, by providing intensity adjustment 101 on the acquired fluoroscopic images 204 and 206, more contrast or a further refined fluoroscopic image is created that more represents and is similar to the DRRs, thereby providing the more accurate initial pose or an initial estimate of the rotation and translation (orientation and position) of the 2D to 3D images. If the optional intensity adjustment at block 101 is not performed, the method may proceed to optional blocks 102 or 103 of the initialization phase or go directly to block 110 in the refinement phase.

Once the optional intensity adjustment at block 101 has been performed, the method may proceed to optional block 102, where the region of interest in the AP image 82 and the lateral image 84 may be adjusted. In this regard, a box or window, not shown, but similar to registration window 114 illustrated in FIG. 13 is initialized over both the AP and lateral images, as well as the corresponding AP and lateral DRRs to identify the region of interest used to compute the later discussed similarity/cost measures. Should the predefined box or window require adjustment, the surgeon may simply adjust the size and positioning of this region or box on the desired area of interest. For example, the surgeon may only wish to capture a single vertebrae within the region of interest, as opposed to capturing multiple vertebrae to insure proper registration on the vertebrae of interest.

Once the region of interest, box or window in these views has been adjusted at block 102, the method may proceed to optional block 103, where alignment of the acquired lateral image with the lateral DRR may be performed using a similarity/cost measure on the adjusted region of interest from block 102. In this regard, the two-dimensional lateral fluoro image 84 may be aligned with the two-dimensional lateral DRR generated at block 98 using normalized mutual information as is known in the art. By aligning both the two-dimensional DRR and the two-dimensional fluoro lateral image, updated or refined rotation and X/Y translation information (orientation and position) is generated for use later during the refinement process. This process is different from the subsequent refinement step because the refinement step uses 3D image data and not the 2D DRR image. Using 3D DRR image data allows the image to slightly change during the 2D to 3D registration process, as opposed to using 2D DRR image data, which does not change to provide a quick estimate of angle and X/Y translation (orientation and position) that may then be used as a beginning or starting point in the later refinement process, if desired.

The alignment of the lateral image data with the lateral DRR is performed because of how the image data is captured between the CT imaging device and the fluoro imaging device. Specifically, during the CT scanning process the patient is scanned supine or face-up. However, when the patient is in the OR and the fluoroscopic image is captured, the patient is typically positioned posteriorly or on their stomach. The difference in the two positions creates a difference angle about the lateral axis, which can affect the later refinement step. By lining up both the 3D image data from the CT scan and the 2D image data from the fluoroscope, via aligning the lateral image with lateral DRR at optional step 103, the image data is already lined up and adjusted to perform the 2D to 3D registration in the refinement step.

From the initialization phase, the process proceeds to block 110, where refined 2D to 3D registration is performed using the position and orientation information calculated in the initialization phase as a starting point. The refinement process uses at least two similarity and/or cost measures (similarity/cost measures) selected from normalized mutual information algorithms, mutual information algorithms, gradient difference algorithms, gradient algorithms, line contour algorithms, surface contour algorithms, and pattern intensity algorithms as known in the art. The similarity/cost measures are selected from generally two types of registration processes, which include the above-noted algorithms. These processes are either image-based or model-based. The image-based registration process is based on the two-dimensional fluoroscopic images and utilizes pattern or image intensity algorithms or is based upon identifying features within the objects. These features utilize known line contour algorithms or gradient algorithms. The model-based registration process is based upon the 3D captured data, such as the CT or MRI data. This process generally includes obtaining surface models of the area of interest, based upon the 3D data and then generating projection rays based on the contour in the fluoroscopic images. A match in three-dimensional space is performed using the rays that become tangent to the surface model. This type of procedure is generally known as a contour-based or surface contour algorithm.

Further examples of various similarity or cost measures are set out in "Providing Visual Information to Validate 2-D to 3-D Registration," André Guéziec, Kenong Wu, Alan Kalvin, Bill Williamson, Peter Kazanzides, and Robert Van Vorhis, Medical Image Analysis 4 (2000) 357-374; "A Comparison of Similarity Measures for Use in 2-D-3-D Medical Image Registration," Graeme P. Penney, Jürgen Weese, John A. Little, Paul Desmedt, Derek L. G. Hill, and David J. Hawkes, IEEE Transactions on Medical Imaging, vol. 17, no. 4, August 1998; and "Validation of a Two to Three-Dimensional Registration Algorithm for Aligning Pre-Operative CT Images and Intraoperative Fluoroscopy Images," Graeme P. Penney, Phillip G. Batchelor, Derek L. G. Hill, and David J. Hawkes, Med. Phys. 28, June 2001, pages 1024-1032, each of which are hereby incorporated by reference.

At least two of the similarity/cost measures are then selected to be used to provide a more robust and accurate registration process. The two selected generally complement one another. In order to optimize the similarity/cost measures, either a multi-stage steepest ascent algorithm, a steepest ascent algorithm, or a gradient-based optimization algorithm, is performed, as is known in the art. In other words, the registration process involves selecting at least two of the known similarity or cost measure algorithms and then optimizing the selected algorithms using one of the known optimization algorithms, such as the steepest ascent algorithm, multi stage steepest ascent algorithm or the gradient-based optimization algorithm.

Initially, before active refinement registration begins, the surgeon may adjust the registration window 114 at block 112. In this regard, the registration window 114, as illustrated in FIG. 13, is positioned about the common coordinate or center point 116, identified in each image, based upon the surgeon's prior selections. The registration window 114 is the region that is used to compute the registration. That is, the image data within the registration window 114 is used for registration, while the information outside the registration window 114 is ignored. Generally, this registration window 114 will not be adjusted, however, the surgeon may adjust the registration window 114, so that it only captures the single vertebrae or body of interest. In other words, if the registration window 114 encompasses two whole vertebrae, which look substantially similar, there is potential for the registration process to select the incorrect vertebrae. Therefore, it is generally desirable to have the registration window 114 sized to only encompass the single vertebrae of interest. Thus, the anatomical landmarks or points within the registration window 114 are only used for the registration process. Essentially, what has been done by selecting the center of vertebrae is that this provides the registration algorithm and initialization on where the mathematical iterations will actually start.

Figure 14:
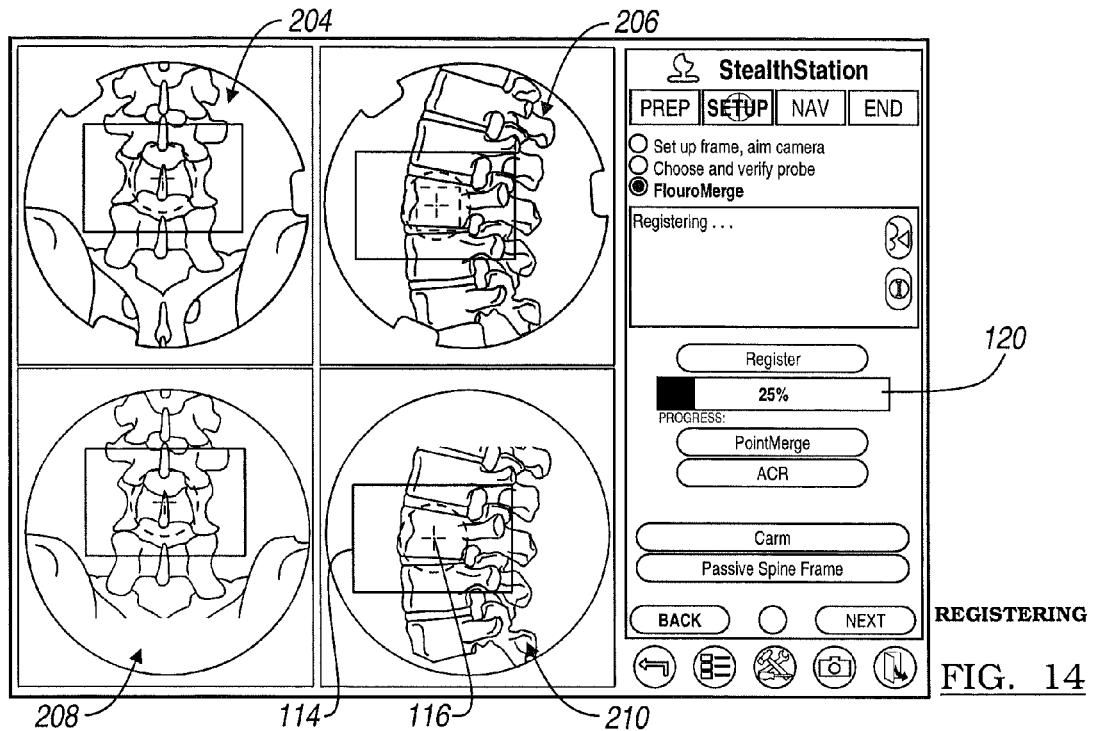
Figure 15:
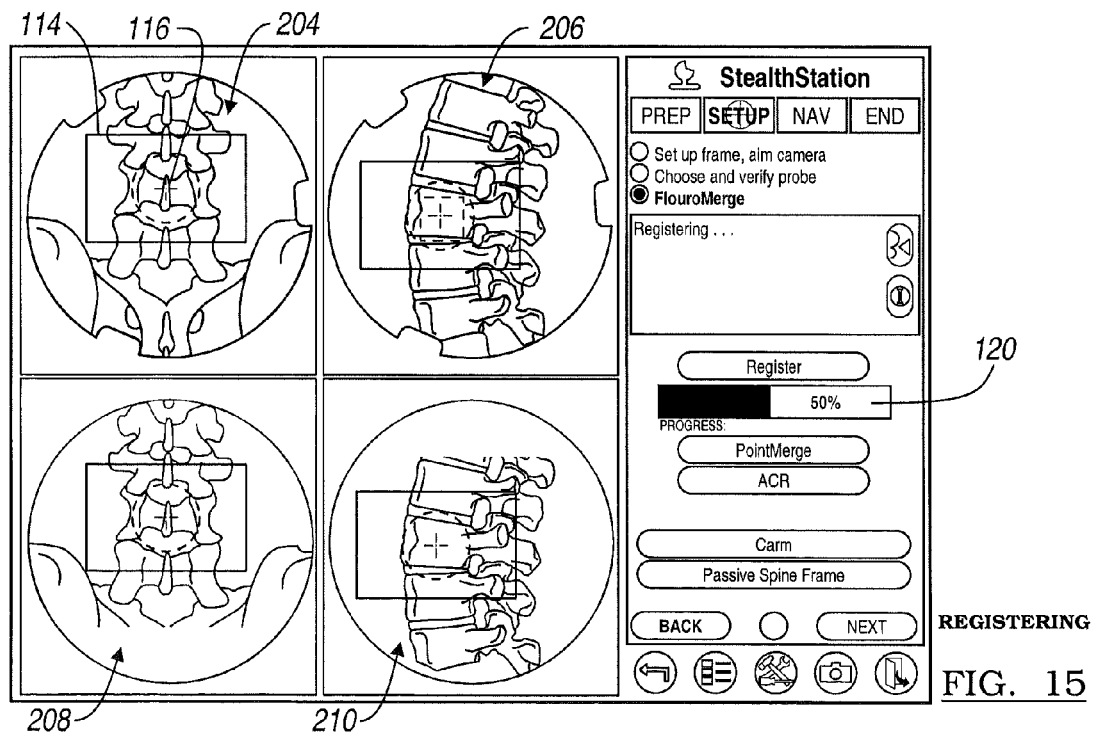
Figure 16:
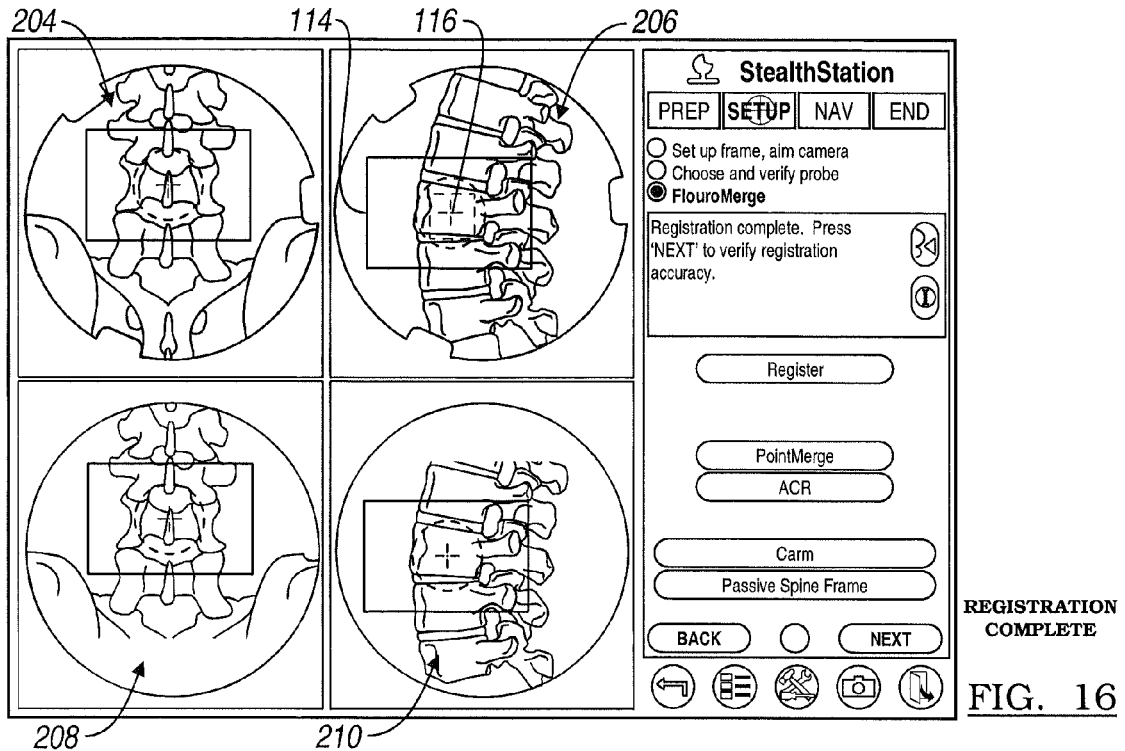

With the registration window selected at block 112, the register button 118 is actuated to start the registration process. The registration process generally takes one to five minutes and the system can be set to stop the calculations at the end of three minutes, thereby providing fast and efficient 2D to 3D registration in an accurate manner. Alternatively, an adjustment button on the screen may be provided to allow the surgeon to select the amount of time in which the registration process should run. This could be implemented, via a slide bar or other type adjustment device. As shown in FIG. 14, a window 120 identifies that the registering technique is 25% completed. During the registration, the actual images will be moving slightly, however, they will not move significantly, since the DRRs are fairly accurate, based on the initial orientation knowledge. FIG. 15 illustrates the registration process at 50% complete in window 120. FIG. 16 illustrates the completed registration.

Again, the registration at block 110 is part of the refinement process, where the software uses image matching algorithms to refine the initial registration. The software changes the position and orientation to minimize the difference between the DRRs and the actual radiographs, thus refining the registration. In this refinement process, similarity and/or cost measures are used to tell how well the image is matched. The iterative refinement algorithm changes position and orientation parameters simultaneously to maximize the similarity between the DRRs and the actual radiographs. The similarity measures used may be the normalized mutual information, mutual information, gradient difference algorithm, surface contour algorithm, and pattern intensity measures.

An exemplary registration process using normalized mutual information (NMI) and pattern intensity (PI) in terms of the known mathematical algorithms is as follows:

Given two images $A(x)$ and $B(y)$, we want to find the rigid transformation $T:x \rightarrow y$ such that:

$$T = \mathrm{argmax}\_TS(A(x), B(T(x))) \text{ for some similarity measure } S(.)[\text{nmi or pi}].$$

The 2D/3D registration 70 uses two similarity measures, normalized mutual information and pattern intensity. The use of both provides greater robustness to the local maxima of an individual measure.

Normalized mutual information of two images, $A(x)$ and $B(y)$, is given as:

$$\mathrm{NMI}(A,B) = [H(A) + H(B)] / H(A,B),$$

where $H(A)$ and $H(B)$ are the entropy of the corresponding images and $H(A,B)$ is the joint entropy.

Pattern intensity (PI) is given as:

$$\mathrm{PI}(A,B) = \mathrm{sum}\_x \mathrm{sum}\_(y \text{ such that } \mathrm{dist}(x,y) \leq r) \mathrm{sigma}^2 / [\mathrm{sigma}^2 + (I\_\mathit{diff}(x) - I\_\mathit{diff}(y))^2],$$

where $I\_\mathit{diff}$ is the difference image between A and B.

A more detailed discussion of pattern intensity is set out in "Validation of a two-to three-dimensional registration algorithm for aligning preoperative CT images and intraoperative fluoroscopy images", Graeme P. Penney, Phillip G. Batchelor, Derek L. G. Hill, and David J. Hawkes, Med. Phys. 28, June 2001, pages 1024-1032, which is hereby incorporated by reference.

In order to optimize these particular similarity measures, a multi-stage steepest ascent algorithm with successively smaller step sizes for each stage is used. The steepest ascent algorithm uses a fixed delta from the current position to evaluate a new candidate to move to if it has a higher value for the similarity measure. The method evaluates several candidates at +/−delta and +/−2×delta and selects the candidate giving highest similarity of each iteration. This enables the algorithm to potentially jump over local minima. Once there is convergence for a given delta, the steepest ascent algorithm is repeated with a smaller value for delta. This increases the resolution and accuracy of the transformation estimates. For example, the delta may start at delta equals 2.0 degrees and 2.0 mm. This search is a discreet parameter space of resolution 2. Then we define delta=1 degree/mm which now searches a finer resolution parameter space and so on. This process changes position and orientation parameters simultaneously to maximize the similarity between the DRRs and the actual radiographs until an acceptable accuracy is met.

It should also be pointed out that multiple registrations may be performed on selected vertebrae. In this regard, the initialization process may be performed on two different vertebrae identified in the same fluoroscopic images. Again, the initialization would include identifying the center of the vertebral bodies of each selected vertebrae. The display 12 can identify the centers differently for each vertebrae selected, such as by using different colors. For example, if registration is performed on two adjacent vertebrae. A center for the first vertebrae will be selected and signified by a first color for the cross-hatch and planes and a center for the other vertebrae will also be selected and identified on the display 12 using another color. Separate DRRs will be generated for each vertebrae of interest and a registration window will be focused on each vertebrae of interest during registration. Thus, the two adjacent vertebrae may each individually be registered providing two different transformations. These two registrations may be shown individually using separate images on the display 12. Alternatively, comparison of the transformations may be performed and if the transformations are similar, one can be selected or an average of the two may be used, thereby resulting in both adjacent vertebrae being registered and displayed on a single view.

Figure 17:
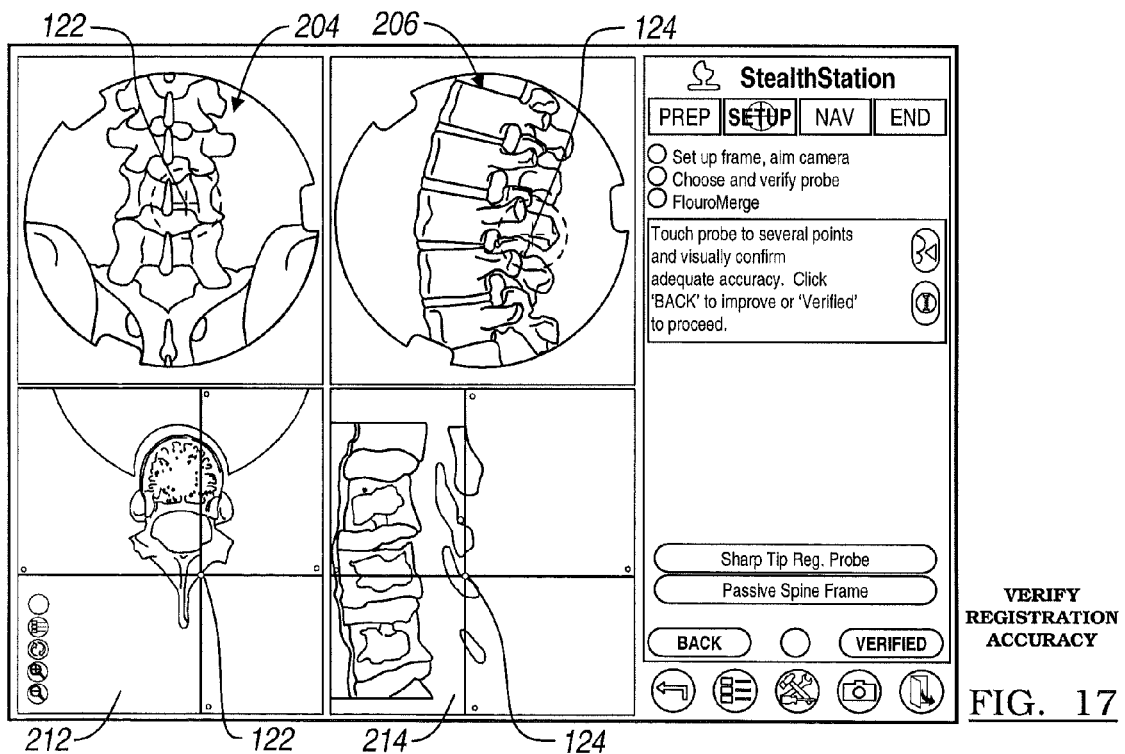
Figure 18:
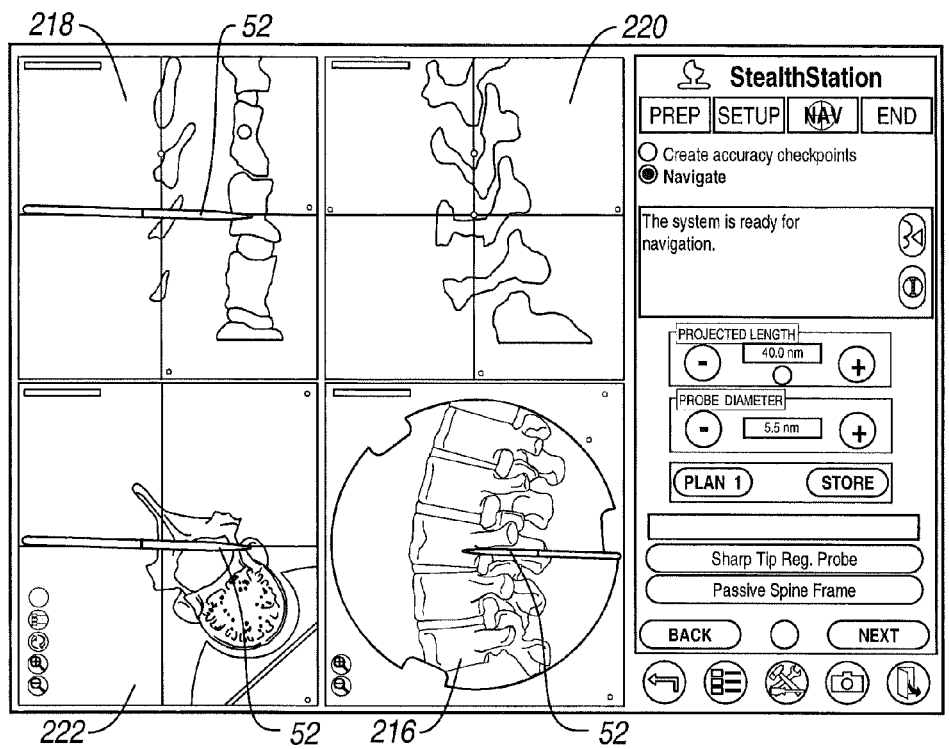

Once the registration has been completed at block 110, the process moves to block 115 where registration accuracy is verified. Once the registration process has been completed at block 110, the display may also illustrate and show a representation on the strength or accuracy of the registration process. This display, for example, may include a graph, that graphs the registration process to illustrate if the registration process was converging to the correct answer. This graph would then provide an indication to the surgeon whether the registration process was accurately performed and achieved. As shown in FIG. 17, the surgeon will select various points in the CT images 212 and 214 at the bottom of the display, such as point 122. This point 122 is then illustrated in the fluoroscopic AP image 204 positioned above. The surgeon can then visually confirm that the position selected in the CT scan 212 matches the corresponding point in the fluoroscopic AP image 204, thereby confirming registration accuracy. The surgeon will also select a point 124 in the other CT image 214, which corresponds to a point 124 in the fluoroscopic lateral image 206. If the surgeon is satisfied with the accuracy, the procedure proceeds to block 120 regarding navigation. If the surgeon is not satisfied with the accuracy, the procedure returns to the register block 110 to perform additional registration to increase the accuracy. At block 120, navigation of both a two-dimensional fluoroscopic image 216 and three-dimensional CT volume images 218, 220 and 222 with the instrument 52, is illustrated in FIG. 18.

By providing both an initialization and refinement processes in the 2D to 3D registration, improved accuracy and efficiency in 2D to 3D registration is realized. By knowing the locations or positions of the CT scan information, as well as the orientation information regarding the fluoroscopic images and then identifying a center, which are subsequently related to the DRRs, the initialization process improves the overall accuracy of the DRRs. In addition, by using two similarity/cost measures, such as the normalized mutual information (NMI) and the pattern intensity (PI) during the registration process, a more robust and efficient registration is achieved that provide results in a faster and more accurate registration process, as opposed to only using NMI or PI for the registration process.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for registering two-dimensional image data of a body of interest with three-dimensional image data of the body of interest comprising:
   loading the three-dimensional image data of the body of interest associated with first body of interest orientation information, wherein the three-dimensional image data is acquired prior to the two-dimensional image data;
   attaching a dynamic reference frame to the body of interest;
   acquiring the two-dimensional image data of the body of interest including the attached dynamic reference frame with an imaging device;
   determining a second body of interest orientation information of the body of interest relative to the imaging device; and
   generating, by executing instructions with a processor, a digitally reconstructed radiograph of the loaded three-dimensional image data that substantially corresponds to the two-dimensional image data, including:
      initializing a registration of the loaded three-dimensional image data and the acquired two-dimensional image data by estimating the orientation and position of the body of interest relative to the imaging device based on the first body of interest orientation information and the second body of interest orientation information;
      wherein the digitally reconstructed radiograph includes a view through the three-dimensional image data that is substantially similar to the acquired two-dimensional image data based on the estimated orientation and position of the body of interest to the imaging device; and
   determining a common point in the acquired two-dimensional image data and the digitally reconstructed radiograph; and
   refining the initialized registration of the acquired two-dimensional image data with the loaded the three-dimensional image data using at least the common point information;
   wherein refining the initialized registration included selecting and employing at least two similarity/cost measures selected from a group comprising a normalized mutual information algorithm, a mutual information algorithm, a gradient difference algorithm, a gradient algorithm, a line contour algorithm, a surface contour algorithm, a pattern intensity algorithm.

2. The method of claim 1, further comprising optimizing the selected and employed similarity/cost measures using at least one of an optimization algorithm selected from a group of at least a multi-stage steepest ascent algorithm, a steepest ascent algorithm, a gradient-based optimization algorithm.

3. The method of claim 1, further comprising:
   acquiring the three-dimensional image data of the body of interest and determining a position of the body of interest relative to a three-dimensional imaging device that acquires the three-dimensional image data of the body of interest;
   wherein the determined position of the body of interest relative to the three-dimensional imaging device is the first body of interest orientation information.

4. The method of claim 1, wherein the determined common point is a center of a vertebral body in the two dimensional image data and the loaded three-dimensional image data.

5. The method of claim 1, wherein refining the initialized registration include executing software that provides a matching algorithm to minimize differences between the generated digitally reconstructed radiograph and the acquired two-dimensional image data of the body of interest;
wherein minimizing differences between the digitally reconstructed radiograph and the acquired two dimensional image data includes refining the estimated orientation and position of the body of interest relative to the imaging device to minimize differences between the generated digitally reconstructed radiograph and the acquired two dimensional image data.

6. The method of claim 1, wherein the first body of interest orientation information include at least one of anterior orientation, posterior orientation, right orientation, left orientation, medial orientation, and lateral orientation of the body of interest in the loaded three dimensional image data.

7. The method of claim 1, wherein acquiring the two-dimensional image data of the body of interest includes acquiring a first two-dimensional image of the body of interest and a second two-dimensional image of the body of interest;
wherein the first two-dimensional image and the second two-dimensional image are acquired of the body of interest by moving the imaging device from a first position while acquiring the first two-dimensional image data to a second position different from the first position while acquiring the second two-dimensional image data.

8. A method for registering two-dimensional image data of a body of interest with three-dimensional image data of the body of interest, comprising:
loading a pre-acquired three-dimensional image data of the body of interest associated with a first body of interest orientation information, wherein the three-dimensional image data is acquired with a first imaging device and prior to the two-dimensional image data;
acquiring the two-dimensional image data of the body of interest with a second imaging device, wherein acquiring the two-dimensional image data of the body of interest includes acquiring a first two-dimensional image of the body of interest at a first position of the imaging device relative to the body of interest; acquiring a second two-dimensional image of the body of interest with the imaging device at a second position relative to the body of interest different from the first position; and identifying a common point in both of the first two-dimensional image and the second two-dimensional image;
determining a second body of interest orientation information of the body of interest relative to the second imaging device;
initializing a registration of the loaded three-dimensional image data and the acquired two-dimensional image data, including:
estimating an orientation and position of the body of interest relative to the second imaging device based on the first body of interest orientation information and the second body of interest orientation information; and
generating a digitally reconstructed radiograph of the three-dimensional imaging data that substantially corresponds to the view of the acquired two-dimensional image data based on the estimated orientation and position of the body of interest relative to the second imaging device; and
refining the initialized registration of the acquired two-dimensional image data with the loaded three-dimensional image data by executing matching algorithms with a processor;
wherein executing the matching algorithms includes executing at least one similarity/cost measure selected from a group comprising a normalized mutual information algorithm, a mutual information algorithm, a gradient difference algorithm, a gradient algorithm, a line contour algorithm, a surface contour algorithm, and a pattern intensity algorithm;
wherein the identified common point in the first two-dimensional image and the second two-dimensional image is identified by sizing an atlas map to the imaged body of interest in the first two-dimensional image and the second two-dimensional image prior to user input.

9. The method of claim 8, further comprising:
confirming the estimated common point by a user input after sizing the atlas map to the imaged body of interest to identify the common point.

10. A method for registering two-dimensional image data of a body of interest with three-dimensional image data of the body of interest, comprising:
loading the three-dimensional image data of the body of interest associated with first body of interest orientation information, wherein the three-dimensional image data is acquired prior to the two-dimensional image data;
acquiring the two-dimensional image data of the body of interest with an imaging device;
determining a second body of interest orientation information of the body of interest relative to the imaging device; and
generating, by executing instructions with a processor, a digitally reconstructed radiograph of the loaded three-dimensional image data that substantially corresponds to the two-dimensional image data, including:
initializing a registration of the loaded three-dimensional image data and the acquired two-dimensional image data by estimating the orientation and position of the body of interest relative to the imaging device based on the first body of interest orientation information and the second body of interest orientation information;
wherein the digitally reconstructed radiograph includes a view through the three-dimensional image data that is substantially similar to the acquired two-dimentional image data based on the estimated orientation and position of the body of interest to the imaging device; and
determining a common point in the acquired two-dimensional image data and the digitally reconstructed radiograph; and
refining the initialized registration of the acquired two-dimensional image data with the loaded the three-dimensional image data using at least the common point information;
wherein acquiring the two-dimensional image data of the body of interest with a second imaging device includes:
tracking an orientation and position of the second imaging device;
tracking an orientation and position of the body of interest;
determining an orientation and position of the body of interest relative to the second imaging device based upon the tracked orientation and position of the second imaging device and the tracked orientation and position of the body of interest.

11. The method of claim 10, wherein tracking the position of the body of interest includes tracking a location of a dynamic reference frame attached to the body of interest;
wherein estimating an orientation and position of the body of interest relative to the second imaging device includes estimating an orientation and position of the body of interest while acquiring the pre-acquired three-dimensional image data of the body of interest;
wherein the estimated orientation and position of the body of interest is based upon the estimated orientation and position of the body of interest relative to the dynamic reference frame for generating the digitally reconstructed radiograph.

12. The method of claim 11, further comprising:
identifying a digitally reconstructed radiograph common point in the generated digitally reconstructed radiograph that is substantially identical to the common point identified in the acquired two-dimensional image data.

13. The method of claim 8, further comprising:
changing the position and orientation of at least one of the acquired two-dimensional image data and the generated digitally reconstructed radiographs to minimize differences between the generated digitally reconstructed radiographs and the acquired two-dimensional image data based upon executing the at least one similarity/cost measure.

14. The method of claim 13, further comprising:
performing, prior to the refining the initialized registration, at least one of adjusting the intensity of the acquired two-dimensional image data, adjusting a region of interest in the acquired two-dimensional image data, aligning the acquired two-dimensional image data with the generated digitally reconstructed radiograph, adjusting a registration window relative to the acquired two-dimensional image data.

15. A method for registering two-dimensional image data of a body of interest with three-dimensional image data of the body of interest, comprising:
loading a pre-acquired three-dimensional image data of the body of interest, wherein the pre-acquired three-dimensional image data of the body of interest is acquired with a first imaging device with the body of interest at a first body of interest position and orientation relative to the first imaging device, wherein the first body of interest position and orientation is saved and associated with the pre-acquired three-dimensional image data as first body of interest orientation information;
tracking a location of the body of interest with a tracking device associated with the body of interest;
tracking a location of a second imaging device;
acquiring the two-dimensional image data of the body of interest with the second imaging device while tracking the location of the second tracking device, wherein the two-dimensional image data includes at least a first two-dimensional image of the body of interest at a first angle relative to the body of interest and a second two-dimensional image of the body of interest at a second angle relative to the body of interest that is different from the first angle;
determining a second body of interest orientation information of the body of interest relative to the second imaging device based upon the tracked location of the body of interest and the tracked location of the second imaging device; and
registering the loaded three-dimensional image data and the acquired two-dimensional image data with at least a two step process, wherein the two step process includes,
performing an initial registration at least by estimating an orientation and position of the body of interest relative to the second imaging device based on the first body of interest orientation information and the tracked location of the body of interest with the tracking device and then generating at least one digitally reconstructed radiograph using the three-dimensional image data that substantially corresponds to the view of the first two-dimensional image data or the second two-dimensional image data based on the estimated orientation and position of the body of interest relative to the second imaging device; and
refining the performed initial registration of the acquired two-dimensional image data with the loaded three-dimensional image data by executing refinement algorithms with a processor.

16. The method of claim 15, wherein the second angle relative to the body of interest is different by about 90 degrees from the first angle relative to the body of interest.

17. The method of claim 15, further comprising at least one of:
adjusting an intensity of histogram of the acquired two-dimensional image data;
adjusting a region of interest in the acquired two-dimensional image data;
aligning at least one of the first two-dimensional image of the body of interest at a first angle relative to the body of interest and the two-dimensional image of the body of interest to the respective generated digitally reconstructed radiograph.

18. The method of claim 17, wherein aligning at least one of the first two-dimensional image of the body of interest and the second two-dimensional image of the body of interest to the respective generated digitally reconstructed radiographs wherein the generated digitally reconstructed radiograph is two-dimensional and remains unchanged when aligned.

19. The method of claim 15, wherein refining the performed initial registration of the acquired two-dimensional image data with loaded the three-dimensional image data by executing refinement algorithms with a processor includes moving at least one of the generated digitally reconstructed radiograph and the acquired two-dimensional image data to minimize differences between the generated digitally reconstructed radiograph and the acquired two-dimensional image data;
verifying the registration by selecting points in the loaded three-dimensional image data and illustrating, based on the refined registration, points in the two-dimensional image data.

20. The method of claim 15, further comprising:
displaying at least one of the acquired two-dimensional image data and the three-dimensional image data that are registered together; and
navigating a procedure relative to the body of interest including illustrating a location of an instrument on a display device superimposed on the displayed at least one of the acquired two-dimensional image data and the three-dimensional image data.

* * * * *